(12) United States Patent
Stewart et al.

(10) Patent No.: US 11,977,358 B2
(45) Date of Patent: May 7, 2024

(54) SYSTEMS AND METHODS FOR DYNAMIC BIOMETRIC CONTROL OF IOT DEVICES

(71) Applicants: Robin H. Stewart, Woodbridge, VA (US); Qiliang Li, Fairfax, VA (US)

(72) Inventors: Robin H. Stewart, Woodbridge, VA (US); Qiliang Li, Fairfax, VA (US)

( * ) Notice: Subject to any disclaimer, the term of this patent is extended or adjusted under 35 U.S.C. 154(b) by 372 days.

(21) Appl. No.: 17/404,617

(22) Filed: Aug. 17, 2021

(65) Prior Publication Data
US 2023/0056100 A1 Feb. 23, 2023

(51) Int. Cl.
*G05B 13/02* (2006.01)
*A61B 5/00* (2006.01)
(Continued)

(52) U.S. Cl.
CPC ........ *G05B 13/0265* (2013.01); *A61B 5/0022* (2013.01); *G06N 20/00* (2019.01);
(Continued)

(58) Field of Classification Search
CPC ................ G05B 13/0265; G05B 15/02; G05B 2219/2642; A61B 5/0022; A61B 5/02055; A61B 5/021; A61B 5/02416; A61B 5/14532; A61B 5/14551; A61B 2503/12; A61B 5/165; A61B 5/4836; A61B 5/486; A61B 5/7267; A61B 5/6823; A61B 5/6824; A61B 5/6826; A61B 2560/0223;
(Continued)

(56) References Cited

U.S. PATENT DOCUMENTS

| 2007/0173733 A1* | 7/2007 | Le | A61B 5/369 |
| | | | 600/544 |
| 2010/0332842 A1* | 12/2010 | Kaloboukis | G06Q 30/02 |
| | | | 707/769 |

(Continued)

OTHER PUBLICATIONS

Swanson, R., Lamb, M., Correia, C. M., Sivanandam, S., Kutulakos, K. (2021). Closed loop predictive control of adaptive optics systems with Convolutional Neural Networks. Monthly Notices of the Royal Astronomical Society, 503(2), 2944-2954. https://doi.org/10.1093/mnras/stab632 (Year: 2021).*

*Primary Examiner* — Thomas C Lee
*Assistant Examiner* — Tyler Dean Hedrick
(74) *Attorney, Agent, or Firm* — Monarch IP Group, PLLC; April M. Mosby

(57) ABSTRACT

Systems and methods of dynamic IoT device regulation and control can aid in shifting a user's emotional state from a first state of mind to a preferred second state of mind, using the user's biomarker response to device settings. Particularly, an IoT device controller may be embedded within a wearable device that is wirelessly connected to a computing device and one or more IoT devices. Initially, each wearable device can be calibrated, wherein a matrix of sensed user biomarker responses can be generated. In some embodiments, the system continuously monitors user biomarkers to detect which physiological state exists. When the user enters into the first physiological/psychological state, the system can adjust each IoT device to align with the second state. When the system detects that the user biomarker response has not shifted, the system can continuously adjust IoT settings based upon a learning algorithm having monitored user biomarkers as input.

20 Claims, 8 Drawing Sheets

(51) Int. Cl.
*A61B 5/0205* (2006.01)
*A61B 5/024* (2006.01)
*G06N 20/00* (2019.01)
*G16Y 30/00* (2020.01)
A61B 5/021 (2006.01)
A61B 5/145 (2006.01)
A61B 5/1455 (2006.01)

(52) U.S. Cl.
CPC .......... *G16Y 30/00* (2020.01); *A61B 5/02055* (2013.01); *A61B 5/021* (2013.01); *A61B 5/02416* (2013.01); *A61B 5/14532* (2013.01); *A61B 5/14551* (2013.01); *A61B 2503/12* (2013.01)

(58) Field of Classification Search
CPC ...... A61B 5/681; G06N 20/00; G06N 3/0464; G16Y 30/00
See application file for complete search history.

(56) References Cited

U.S. PATENT DOCUMENTS

| | | | |
|---|---|---|---|
| 2015/0048178 A1* | 2/2015 | Edwards | G06F 3/011 |
| | | | 239/128 |
| 2017/0270922 A1* | 9/2017 | Fu | G10L 17/22 |
| 2019/0159736 A1* | 5/2019 | Byron | G16H 50/50 |
| 2019/0206423 A1* | 7/2019 | Winton | G10L 25/63 |
| 2020/0056902 A1* | 2/2020 | Woo | A61B 5/18 |
| 2020/0302310 A1* | 9/2020 | Woiceshyn | G06K 7/1413 |
| 2022/0022808 A1* | 1/2022 | Moros Ortiz | G16Y 40/20 |
| 2023/0052474 A1* | 2/2023 | Rajanna | B60W 50/14 |

\* cited by examiner

SYSTEMS AND METHODS FOR DYNAMIC BIOMETRIC CONTROL OF IOT DEVICES

CROSS REFERENCE TO RELATED APPLICATIONS

This present application relates to commonly-owned U.S. patent application Ser. No. 16/928,464, entitled "Systems and Methods for Dynamic Biometric Detection and Response," naming Robin Hardie Stewart and Qiliang Li as the inventors, filed Jul. 14, 2020, which is the currently application; the contents of which are incorporated by herein by reference in its entirety. Additionally, the present application relates to commonly-owned U.S. Patent Application Ser. No. 62/922,623, entitled "Wireless Communicating, Detecting, Conveyance, Technology Bands," naming Robin Hardie Stewart and Qiliang Li as the inventors, filed Aug. 20, 2019, which is the currently application; the contents of which are incorporated by herein by reference in its entirety. Further, the present application relates to commonly-owned U.S. Patent Application Ser. No. 62/973,470, entitled "Wireless Prescription and Medical Communicating Band," naming Robin Hardie Stewart and Qiliang Li as the inventors, filed Oct. 21, 2019; which is also a currently application from, the contents of which are incorporated by herein by reference in its entirety.

BACKGROUND

In light of extreme shifts in the national economy, weather, and health, most people can find themselves in a stressful state of mind. Stress and anxiety are the mental states of emotional strain that can result from adverse and overly demanding circumstances. Consquentially, stress and anxiety can cause various health deficiencies from a slight annoyance to depression or worse yet, heart disease, ultimately leading to death. Fortunately, we have resources through stress management techniques that can enable a person to shift from a stressful state to a calm peaceful manner. There are a great variety of therapies that help people to control their level of stress. However, With the number of techniques that are available a person may be at a loss as to which technique should be applied specifically for them. A person may not have the expertise to know all of the psychological factors, analysis, and assessment.

Professional counseling can help. There are various types of counseling programs that address changing the state of your thinking. However, it becomes problematic, when a person is not feeling well due to the lack of energy that accompanies stress, anxiety, and depression. Particularly, a person may not have the energy to transition out of a problematic psychological state to one that is bright and cheerful. Some counselors provide audio therapy, however this is not always readily available and can prove to be quite expensive.

It is within this context that the embodiments arise.

SUMMARY

Embodiments of a system and method for dynamic IoT device regulation and control are provided. It should be appreciated that the present embodiment can be implemented in numerous ways, such as a process, an apparatus, a system, a device, or a method. Several inventive embodiments are described below.

In some embodiments, a system and method of dynamic IoT device regulation and control can aid in shifting a user's emotional state from a first physiological state to a preferred second physiological state, using the user's biomarker response to IoT device settings. For example, the regulation and control system disclosed herein can aid in shifting a person from an anxious to a calm state of mind by adjusting various settings of one or more IoT devices, such as an image shown on a display or an audio recording, for example. Particularly, in some embodiments, an IoT device controller may be embedded within a wearable device that is wirelessly connected to a computing device and one or more IoT devices. In some embodiments, the system and method may include sensing the biomarkers of the user to identify each physiological state. For example, the system may include the step of retrieving the user's temperature from a thermometer; retrieving the user's blood pressure from a sensing unit having a deep learning algorithm associated with monitoring heart rate; retrieving the user's blood oxygen level from a pulse oximeter blood oxygen sensor; retrieving the user's blood glucose level from a non-invasive glucose monitor; and/or retrieving the user's pulse from an optical heart sensor. Initially, the method may include calibrating each wearable device during a period of time, wherein a matrix of sensed user biomarker responses and corresponding IoT device settings is generated. In some embodiments, the system can continuously monitor user biomarkers to detect which physiological state exists using a dynamic IoT device setting module located within a wearable client device. When the user enters into the first physiological state, the system can adjust each IoT device setting to be equal to settings associated with the second physiological state based upon the user profile matrix. When the system detects that the user biomarker response has not shifted to the second physiological state, the dynamic IoT device setting module can adjust IoT settings based upon a learning algorithm having continuous monitored user biomarkers as input. For example, the system and method may include monitoring user biomarker response using advanced machine-learning algorithms, including principal component analysis and neural network computations; and identifying repetitive responses to select one or more IoT device settings that correspond with the preferred physiological state as a form of predictive analysis.

In some embodiments, a monitoring system having dynamic biometric regulation and control is provided. The monitoring system may include a processor coupled to a memory; wherein the processor is operable to calibrate a dynamic IoT device setting module with user biomarker response to one or more IoT device settings defined within a user profile matrix. The processor may also be operable to monitor one or more user biomarkers and stored these in a user profile matrix. In particular, the processor may be able to sense one or more to the following: the user's temperature from a thermometer, the user's blood pressure from a sensing unit having a deep learning algorithm associated with monitoring heart rate, the user's blood oxygen level from a pulse oximeter blood oxygen sensor, the user's blood glucose level from a non-invasive glucose monitor, the user's pulse from an optical heart sensor, and the like. The processor may be further operable to detect a first physiological state based upon the user profile matrix. When the processor detects the existence of the first physiological state, processor may be further operable to adjust one or more IoT device settings to settings associated with a second physiological state. As feedback, the processor may be further operable to sense user biomarker response to the adjusted settings. If the processor detects that the user biomarker response to the adjusted one or more IoT device settings does not place the user in the second physiological state, the processor may be further operable to adjust the one or more IoT devices based upon a learning algorithm until alignment of the sensed biomarkers with the second physiological state occurs. For example, the processor may be operable to monitor the user's biomarker response using advanced machine-learning algorithms, including principal component analysis and neural network computations; and identifying repetitive responses to select one or more IoT device settings that correspond with the preferred physiological state as a form of predictive analysis.

In some embodiments, a tangible, non-transitory, computer-readable media having instructions whereupon which, when executed by a processor, cause the processor to perform the dynamic biometric regulation and control method described herein. The method may include calibrating a dynamic IoT device setting module with user biomarker response to one or more IoT device settings defined within a user profile matrix. The method may further include continuously monitoring one or more user biomarkers and stored these in a user profile matrix. In particular, the method may include sensing one or more to the following: the user's temperature from a thermometer, the user's blood pressure from a sensing unit having a deep learning algorithm associated with monitoring heart rate, the user's blood oxygen level from a pulse oximeter blood oxygen sensor, the user's blood glucose level from a non-invasive glucose monitor, the user's pulse from an optical heart sensor, and the like. The method may also include detecting a first physiological state based upon the user profile matrix. When there is no evidence of the existence of the first physiological state detected, method may include adjusting one or more IoT device settings to settings associated with a second physiological state. As feedback, the method may include sensing user biomarker response to the adjusted settings. When a lack of alignment to the second physiological state exists, the method may include detects further adjusting of one or more IoT devices based upon a learning algorithm until alignment of the sensed biomarkers with the second physiological state occurs. For example, the method may include monitoring the user's biomarker response using advanced machine-learning algorithms, including principal component analysis and neural network computations; and identifying repetitive responses to select one or more IoT device settings that correspond with the preferred physiological state as a form of predictive analysis.

Other aspects and advantages of the embodiments will become apparent from the following detailed description taken in conjunction with the accompanying drawings which illustrate, by way of example, the principles of the described embodiments.

BRIEF DESCRIPTION OF THE DRAWINGS

The described embodiments and the advantages thereof may best be understood by reference to the following description taken in conjunction with the accompanying drawings. These drawings in no way limit any changes in form and detail that may be made to the described embodiments by one so skilled in the art without departing from the spirit and scope of the described embodiments.

DETAILED DESCRIPTION

Figure 1:
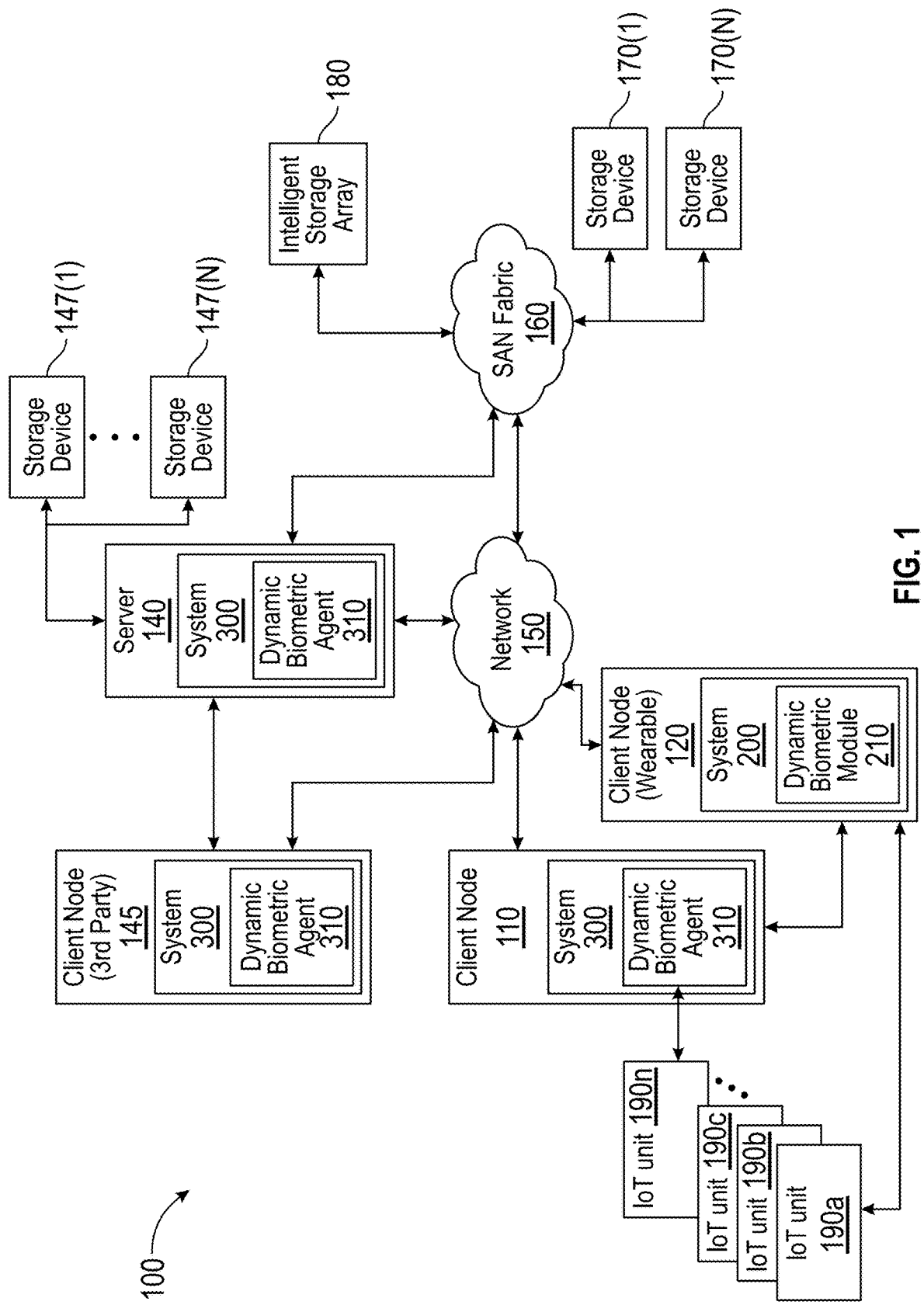
FIG. 1 is a system diagram of an exemplary network incorporating the systems and methods of dynamic biometric regulation and control, in accordance with some embodiments.

The following embodiments describe a system and method for dynamic IoT device regulation and control. It can be appreciated by one skilled in the art, that the embodiments may be practiced without some or all of these specific details. In other instances, well known process operations have not been described in detail in order not to unnecessarily obscure the embodiments.

Systems and methods of dynamic biometric regulation and control of one or more IoT devices can aid in shifting a user's emotional state from a first physiological state to a preferred second physiological state, using the user's biomarker response to IoT device settings. For example, the regulation and control system disclosed herein can aid in shifting a person from an anxious to a calm state of mind by adjusting various settings of one or more IoT devices, such as an image shown on a display or an audio recording, for example. Particularly, in some embodiments, an IoT device controller may be embedded within a wearable device that is wirelessly connected to a computing device and one or more IoT devices. In some embodiments, the system and method may include sensing the biomarkers of the user to identify each physiological state. For example, the system may include the step of retrieving the user's temperature from a thermometer; retrieving the user's blood pressure from a sensing unit having a deep learning algorithm associated with monitoring heart rate; retrieving the user's blood oxygen level from a pulse oximeter blood oxygen sensor; retrieving the user's blood glucose level from a non-invasive glucose monitor; retrieving the user's pulse from an optical heart sensor, and the like.

In some embodiments, the method may initially include calibrating each wearable device during a period of time, wherein a matrix of sensed user biomarker responses and corresponding IoT device settings is generated. The system can continuously monitors user biomarkers to detect which physiological state exists using a dynamic IoT device setting module located within the wearable client node. When the user enters into the first physiological state, the system can adjust each IoT device setting to align with the second physiological state based upon the user profile matrix. When the system detects that the user biomarker response has not shifted to the second physiological state, the dynamic IoT device setting module can adjust IoT settings based upon a learning algorithm having continuous monitored user biomarkers as input. For example, the system and method may include monitoring user biomarker response using advanced machine-learning algorithms, including principal component analysis and neural network computations; and identifying repetitive responses to select one or more IoT device settings that correspond with the preferred physiological state as a form of predictive analysis.

Advantageously, the system and method of dynamic biometric regulation of one or more IoT devices can be a wearable platform that intelligently learns patterns in the user's biomarkers, in an effort to detect, treat, and respond to daily physical and mental stress patterns emitted by the user, based upon the user's biomarker response to differing IoT devices. This biofeedback platform can incorporate various forms of psychoacoustics, psycho-imagery, cognitive reframing techniques, and the like to aid in the management and treatment of anxiety, chronic stress, depression, various other emotional and mental disorders/abnormalities. This wearable system and method of dynamic biometric regulation of one or more IoT devices can intuitively deliver a health wellness process to aid in establishing mental and physical wellbeing. In some embodiments, the system and method of dynamic biometric regulation and control can provide a customized plan specifically formulated based upon the user's biometric data. Moreover, some embodiments may include voluntary data sharing and analysis with a professional counselor, physician, and the like. That is, some features included within the system of dynamic IoT device regulation and control may include real-time data sharing, biometric-chart sharing/monitoring, psychoacoustics treatment guidance, psycho-imagery treatment guidance, interactive therapy, health and wellness goal setting (planning), and the like. In congruence with most health and wellness programs, this system can be HIPAA Compliant.

In the following description, numerous details are set forth. It will be apparent, however, to one skilled in the art, that the present invention may be practiced without these specific details. In some instances, well-known structures and devices are shown in block diagram form, rather than in detail, in order to avoid obscuring the present invention.

Some portions of the detailed descriptions, which follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, as apparent from the following discussion, it is appreciated that throughout the description, discussions utilizing terms such as "detecting," "determining," "adjusting," "monitoring," "sensing," "retrieving," "receiving," "storing", or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present invention also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

Reference in the description to "one embodiment" or "an embodiment" means that a particular feature, structure, or characteristic described in connection with the embodiment is included in at least one embodiment of the invention. The phrase "in one embodiment" located in various places in this description does not necessarily refer to the same embodiment. Like reference numbers signify like elements throughout the description of the figures.

Referring to FIG. 1, the system diagram of an exemplary network incorporating the systems and methods of dynamic biometric regulation and control, in accordance with some embodiments, is shown. The networked system includes at least one client node (110, 120), a network 150, at least one server 140, and a database (not shown in FIG. 1 but shown FIGS. 2 and 3). As shown in FIG. 1, the exemplary network architecture 100 may include client nodes such as computing devices (110) and wearable computing devices (120), in direct communication with one another and in communication with the server 140 through network 150. Each client node (110, 120) may possess a dynamic biometric module 210, while each server node (computing device) 140 may possess a dynamic biometric agent 310 (to be described in detail further with reference to FIG. 3). In some embodiments, the client node 110 may possess a dynamic biometric agent 310 (as shown in FIG. 1). Additionally in some embodiments, third party client nodes 145 may couple to the server node 140 directly or indirectly through network 150 for the purpose of monitoring user biomarker response and controlling IoT device settings. For example, when a professional clinician, psychologist, or physician has been granted access to the user's profile matrix of biomarker responses. One or more IoT devices, such as an audio stereo system and speaker (for example) may couple to any one of the client nodes (110, 120, 145) to be used as part of the treatment towards shifting the user biomarkers from a first physiological and/or psychological state to a second (preferred) physiological/psychological state. Additionally, the network may include one or more client nodes 145 enabled to couple to any one of the client nodes (110, 120) by way of Bluetooth and Wi-Fi communications to access and retrieve data. For example in observation of a first stressful state, a clinician at client node 145 can access the user profile matrix of client nodes (110, 120) and server 140 and retrieve data (such as sensed vitals) as would be appreciated by one of ordinary skill in the art having the benefit of this disclosure.

In some embodiments, computing devices node 110, 120, with local data store, may couple to the server 140, having its own dynamic biometric agent 310, through network 150 for the purpose of sharing and processing of data. Server 140 may couple to the storage devices 147 (1-N) for reference to prior user profile matrices, medical history data, historical physiological/psychological state data, and versions of other parameters described below. The server 140 may perform further data processing to generate qualitative and quantitative reports based upon user biomarker response, IoT device settings, physiological state data, psychological state data, and/or alerts provided over a predetermined time period. Although not shown, governing authorities, such as state and federal government agencies or private hospitalization institutions and networks may couple a server 140 through network 150 to provide and/or retrieve medically related data. The data provided by these authorities may be used by server 140 (dynamic biometric agent 310) and client nodes (110, 120, 145) (dynamic biometric module 210 and dynamic biometric agent 310) to detect repetitive physiological/psychological patterns within the user's profile matrix, the sensed biomarkers, and the identified user physiological state, in real time as described below. Each client node 110, 120 may include a dynamic biometric module 210, memory (not shown), a processor (not shown, and local data store (not shown) (to be described in detail with reference to FIG. 2).

In some embodiments, the dynamic biometric module 210, having dynamic IoT controller and physiological/psychological state policies, may serve as a device that communicates with the server 140 such that the client (110, 120) performs the method of dynamically adjusting the IoT device settings based upon the user's biomarker response in real-time described more in detail below. In some embodiments, the dynamic biometric module 210 of a user wearing client node 120 may serve as the device that performs both the method of sensing of the user's biomarker response and the method of dynamically adjusting the IoT device settings based upon the user's biomarker response in real-time. In some embodiments, the dynamic biometric module 210 of the client node 110 coupled to the wearable client node 120 may serve as the device that performs the method of dynamically adjusting the IoT device settings based upon the user's biomarker response in real-time, after the dynamic biometric module 210 of the wearable client node 120 performs the method of sensing of the user's biomarker response. In other embodiments, the dynamic biometric agent 310 of client node 110 or server 140, having an dynamic IoT controller and physiological/psychological state policies, may communicate with each client node (110, 120) and serve as the sole agent that performs the method of dynamically adjusting the IoT device settings based upon the user's biomarker response in real-time described herein.

In some embodiments, a third party at client node 145, having dynamic IoT controller and physiological/psychological state policies, may serve as a device that communicates with the server 140 such that the client node 145 performs the method of dynamically adjusting the IoT device settings based upon the user's biomarker response and clinician input in real-time. The client nodes (110, 120, 145), server 140, and the storage devices 147(1-N) may reside on the same LAN, or on different LANs that may be coupled together through the Internet, but separated by firewalls, routers, and/or other network devices. In one embodiment, client nodes 110, 120, 145 may couple to network 150 through a mobile communication network. Client nodes 110, 120, 145 may couple to network 150 through Plain Old Telephone System (POTS). In another embodiment, the client nodes (110, 120, 145), server 140, and the storage device 147(1-N) may reside on different networks. In some embodiments, the server 140 may reside in a cloud network. In some embodiments, the server 140 and the client nodes 110, 120, 145 may access a computer network having distributed ledger technology therein. That is, at least one node within the system 100 can couple directly or indirectly to a plurality of nodes within a distributed ledger network. In the alternative, system 100 may be implemented entirely within a distributed ledger network. Although not shown, in various embodiments, the client nodes 110, 120, 145 may be notebook computers, desktop computers, microprocessor-based or programmable consumer electronics, network appliances, mobile telephones, smart telephones, pagers, radio frequency (RF) devices, infrared (IR) devices, Personal Digital Assistants (PDAs), set-top boxes, cameras, integrated devices combining at least two of the preceding devices, and the like. FIG. 1 illustrates that the dynamic biometric module 210 may also entirely or partially operate to communicate with called party devices having no processing components.

In some embodiments (although not shown), the network 100 may also include at least one dumb terminal, such as a landline, cell phone, pager monitor, and the like. For example, server 140 may also be coupled to a conventional telephone by the Public Switched Telephone Network (PSTN), which couple can couple to network 150.

Figure 6A:
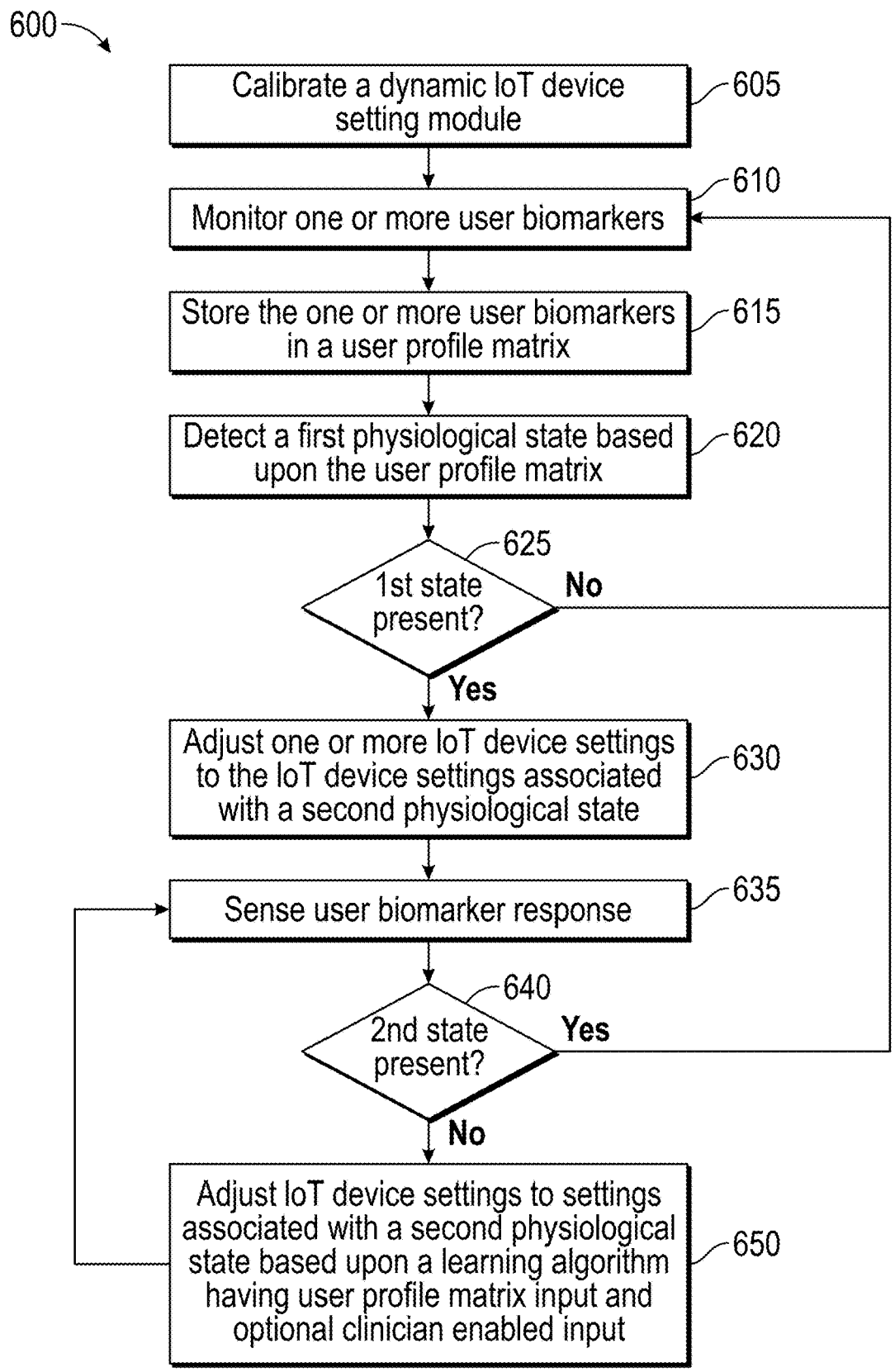
FIG. 6A is an exemplary flow diagram of a method for dynamic biometric regulation and control, in accordance with some embodiments.
Figure 6B:
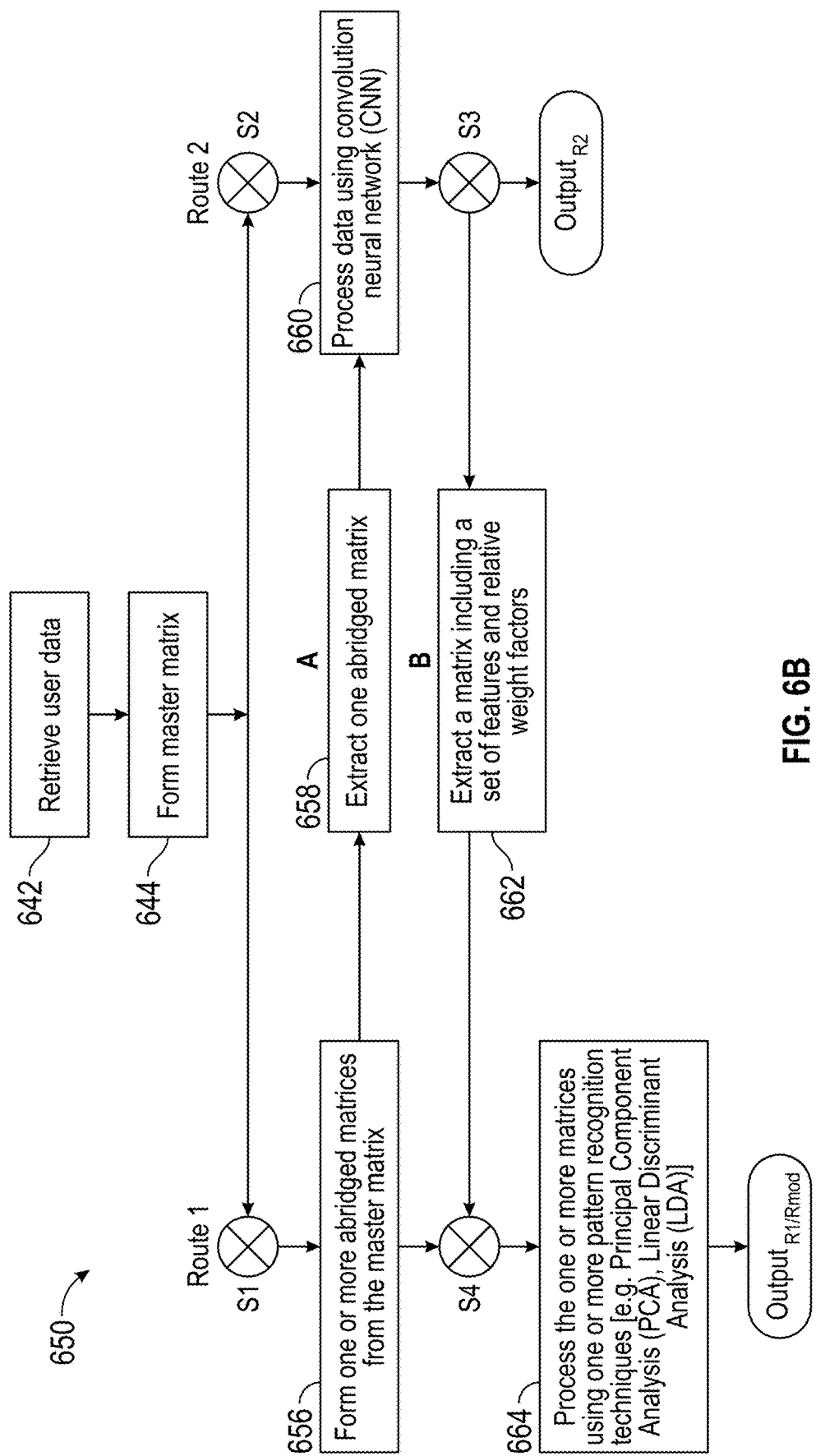
FIG. 6B is an exemplary flow diagram of a method for monitoring user biomarker response using an enhanced machine-learning algorithm to identify repetitive patterns associated with a physiological state of FIG. 6A, in accordance with some embodiments.

All or a portion of network architecture 100 may perform and/or be a means for performing, either alone or in combination with other elements, one or more of the steps disclosed herein (such as one or more of the steps illustrated in FIGS. 6A, 6B). In one example, wearable client node (120) may be programmed with one or more of modules 210 (described in detail below). In another example, computing device 110 may be programmed with one or more of modules 210 or agents 310 (described in detail below). Additionally or alternatively, server 140 may be programmed with one or more of agents 310. Although not shown, in various embodiments, the client node (110) including system 300 may include notebook computers, desktop computers, microprocessor-based or programmable consumer electronics, network appliances, mobile telephones, smart telephones, pagers, radio frequency (RF) devices, infrared (IR) devices, Personal Digital Assistants (PDAs), set-top boxes, cameras, integrated devices combining at least two of the preceding devices, and the like.

Figure 7:
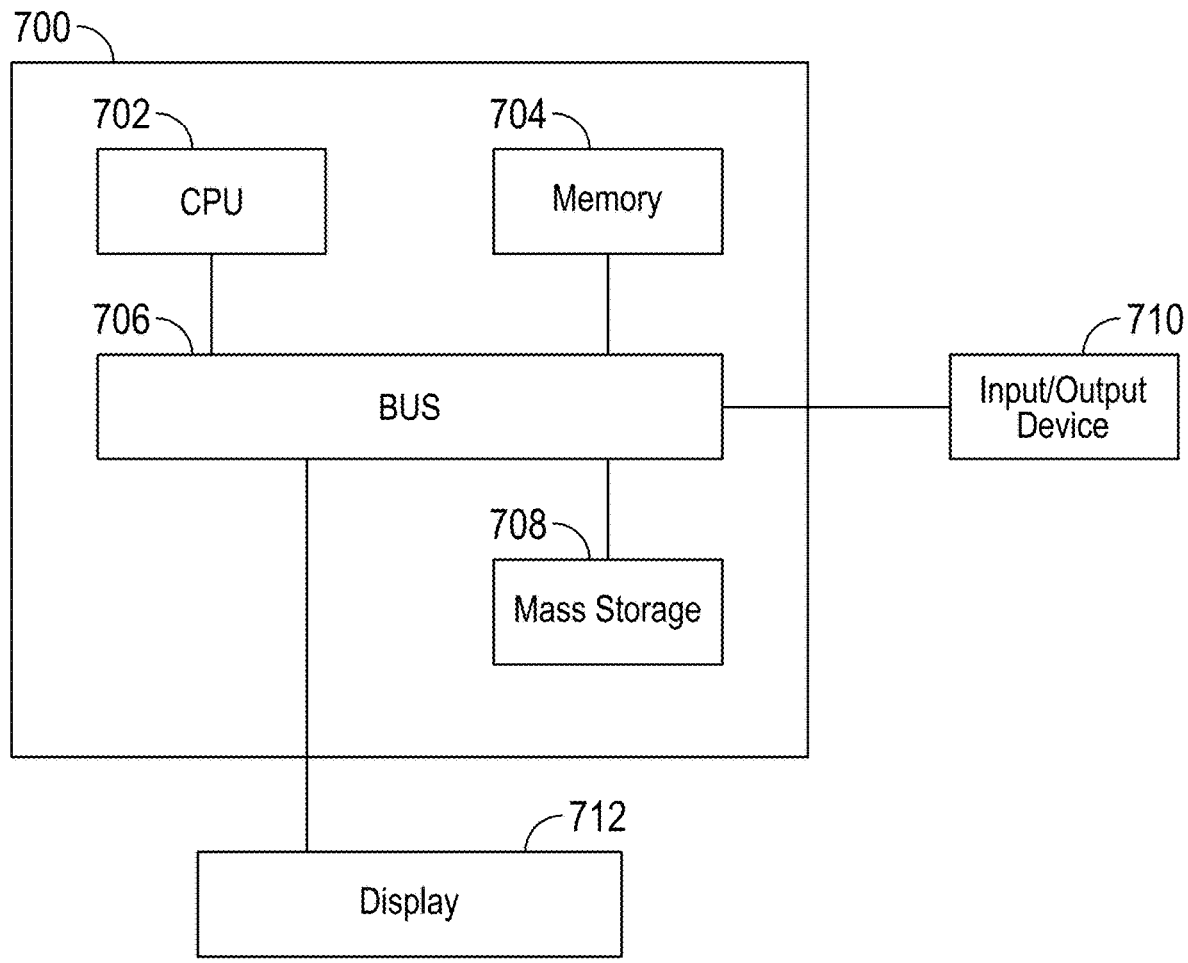
FIG. 7 is an illustration showing an exemplary computing device, which may implement the embodiments described herein.

Client nodes 110, 120, 145 generally represent any type or form of computing device or system, such as exemplary computing system 700 in FIG. 7. Similarly, server 140 generally represents computing devices or systems, such as application servers or database servers, configured to provide various database services and/or run certain software applications. Network 150 generally represents any telecommunication or computer network including, for example, an intranet, a WAN, a LAN, a PAN, or the Internet. In one example, client systems 110, 120, and/or 145 and/or server 140 may include all or a portion of system 200 from FIG. 2. In another example, client systems 110, 120, and/or 145 and/or server 140 may include all or a portion of system 300 from FIG. 3.

The server 140 may comprise a processor (not shown), memory (not shown), and dynamic biometric agent 310. In some embodiments, the server 140 may comprise processing software instructions and/or hardware logic required for dynamic biometric regulation and control according to the embodiments described herein. The server 140 may provide remote cloud storage capabilities for call classifications, call filters, and various types of anomaly policies associated, through the storage device 160 coupled by network 150. In addition the server 140 may provide remote storage capabilities (170(1-N)) for user profile matrix data. Further, server 140 may couple to one or more tape-out devices (not shown) or any other secondary datastore. As such, a database of user profile matrix data and IoT setting/physiological state policies may be stored within a local data store, remote disks, secondary data storage devices, or tape-outs devices (not shown). In some embodiments, the client nodes 110, 120, 145 may retrieve previous results relating to user profile matrix data and IoT setting/physiological state policies relating to user biomarker response patterns from a remote datastore to a local data store (not shown). In other embodiments, the database of physiological state policies, prior physiological state detection results, medical history data, and the like may be stored locally on the client nodes 110, 120, 145, or the server 140. In particular, for remote storage purposes, the local data storage unit (not shown) can be one or more centralized data repositories having mappings of respective associations between each fragment data and its location within remote storage devices. The local data store may represent a single or multiple data structures (databases, repositories, files, etc.) residing on one or more mass storage devices, such as magnetic or optical storage based disks, tapes or hard drives. This local data store may be an internal component of the server 140. In the alternative, the local data store 147 (1-N) also may couple externally to server 140 as shown in FIG. 1, or remotely through a network 160 (storage devices 170(1-N)). Further, the server 140 may communicate with the remote storage devices over a public or private network. Although not shown, in various embodiments, the server 140 may be a notebook computer, desktop computer, microprocessor-based or programmable consumer electronics, network appliance, mobile telephone, smart telephone, radio frequency (RF) device, infrared (IR) device, Personal Digital Assistant (PDA), set-top box, an integrated device combining at least two of the preceding devices, and the like.

In some embodiments, one or more storage devices 147 (1)-(N) may be directly attached to server 140. Storage devices 147(1)-(N) generally represent any type or form of storage device or medium capable of storing data and/or other computer-readable instructions. In certain embodiments, storage devices 147(1)-(N) may represent Network-Attached Storage (NAS) devices configured to communicate with server 140 using various protocols, such as Network File System (NFS), Server Message Block (SMB), or Common Internet File System (CIFS).

Server 140 may also be connected to a Storage Area Network (SAN) fabric 160. SAN fabric 160 generally represents any type or form of computer network or architecture capable of facilitating communication between a plurality of storage devices. SAN fabric 160 may facilitate communication between server 140 and a plurality of storage devices 170(1)-(N) and/or an intelligent storage array 180. SAN fabric 160 may also facilitate, via network 150 and server 140, communication between client systems (110, 120, and 145), and storage devices 170(1)-(N) and/or intelligent storage array 180 in such a manner that devices 170(1)-(N) and array 180 appear as locally attached devices to client systems 110, 120, and 145.

In certain embodiments, and with reference to exemplary computing system 700 of FIG. 6, a communication interface may be used to provide connectivity between each client system 105, 110, and 120 and network 150. Client systems 105, 110, and 120 may be able to access information on server 140 using, for example, a web browser or other client software. Such software may allow client systems 105, 110, and 120 to access data hosted by server 140, storage devices 147(1)-(N), storage devices 170(1)-(N), or intelligent storage array 180. Although FIG. 1 depicts the use of a network (such as the Internet) for exchanging data, the embodiments described and/or illustrated herein are not limited to the Internet or any particular network-based environment.

In at least one embodiment, all or a portion of one or more of the exemplary embodiments disclosed herein may be encoded as a computer program and loaded onto and executed by server 140, storage devices 147(1)-(N), storage devices 170(1)-(N), or intelligent storage array 180, or any combination thereof. All or a portion of one or more of the exemplary embodiments disclosed herein may also be encoded as a computer program, stored in server 140, and distributed to client systems 110, 120, and 145 over network 150.

In operation, the dynamic biometric module 210 within client device 120 may begin a calibration routine for customizing the module 210 with the user's biomarker response to one or more IoT devices and settings thereof to be defined within a user profile matrix. In some embodiments the dynamic biometric module 210 can continuously monitor one or more user biomarkers and store these in a user profile matrix. In particular, the dynamic biometric module 210 may sense one or more to the following: the user's temperature from a thermometer, the user's blood pressure from a sensing unit having a deep learning algorithm associated with monitoring heart rate, the user's blood oxygen level from a pulse oximeter blood oxygen sensor, the user's blood glucose level from a non-invasive glucose monitor, the user's pulse from an optical heart sensor, and the like. The dynamic biometric module 210 may further detect a first physiological state based upon the user profile matrix. When the dynamic biometric module 210 detects the existence of the first physiological state, the dynamic biometric module 210 can adjust one or more IoT device settings to settings associated with a second physiological state. As feedback, the dynamic biometric module 210 may sense the user's biomarker response to the adjusted settings. If the dynamic biometric module 210 detects that the user biomarker response to the adjusted one or more IoT device settings does not place the user in the second physiological state, the dynamic biometric module 210 may further adjust the one or more IoT device settings based upon a learning algorithm (having the user profile matrix as input) until alignment of the sensed biomarkers with the second physiological state occurs. For example, the dynamic biometric module 210 may be operable to monitor the user's biomarker response using advanced machine-learning algorithms, including principal component analysis and neural network computations; and identifying repetitive responses to select one or more IoT device settings that correspond with the preferred physiological state as a form of predictive analysis.

In some embodiments, the dynamic biometric module 210 of client device 120 may be in communication with the dynamic biometric agent 310 of client 110, such that client node 110 issues the control signals to adjust the one or more IoT devices. In some embodiments, the dynamic biometric module/agent (210, 310) of the client device (110 or 120) can communicate with a third party at client node 145 for professional monitoring of the user's biomarker response and development of a treatment plan. Particularly, a waistband (not shown) having a dynamic biometric module that is worn with the band/device (210) can simultaneously record user matrix profile data, in an effort to report real-time usage and body-emitting vitals to be shared and immediately transmitted to secure machine learning/cloud platforms connected through an array of secure, access granted, software and hard-ware linked platforms (to be described in more detail with respect to FIG. 2).

Particularly for example, when the dynamic biometric module 210 senses the biomarkers of user, in some embodiments the dynamic biometric module 210 may retrieve one or more to the following: the user's temperature from a thermistor; the user's blood pressure from a sensing unit having a deep learning algorithm associated with monitoring heart rate; the user's blood oxygen level from a pulse oximeter blood oxygen sensor; the user's blood glucose level from a non-invasive glucose monitor; the user's pulse from an optical heart sensor, and the like. Additionally, the dynamic biometric module 210 may predict user biomarker response along with associated IoT device settings. For example, the dynamic biometric module 210 may monitor the user biomarker response using advanced machine-learning algorithms, including principal component analysis and neural network computations. Moreover, based upon the sensed biomarkers and the user profile matrix, the dynamic biometric module 210 may be operable to detect similar patterns in the user biomarker response to each IoT device and respective setting and to predict IoT device settings in alignment with a preferred physiological state. Finally, the dynamic biometric module 210 may generate physiological state alert for third party notification and/or quantitative analysis at a server.

In some embodiments, the dynamic biometric module 210 may be used to collect and transmit a balanced combination of data associated with the user. For example, dynamic biometric module 210 may collect data relating to the user's biomarkers (e.g. the heartbeat, blood oxygen level, blood pressure, temperature, and the like); and time periods associated with these. The dynamic biometric module 210 can use this data to build an active profile model of user's biomarker response to IoT device settings. Such a model includes intertwined array of the users' measure of central tendency bio-marker indications, user's physiological state data, time parameters, and the like. The parameters of the model can be stored in a matrix of a local database of the dynamic biometric module 210, wherein multiple dimensions can be stored. For example, the following matrix having 72×2850 elements may describe the model for a user.

$$R = \begin{bmatrix} R_{1,1} & R_{1,2} & \cdots & R_{1,2849} & R_{1,2850} \\ R_{2,1} & R_{2,2} & \cdots & R_{2,75} & R_{2,2850} \\ \vdots & \vdots & \ddots & \vdots & \vdots \\ R_{71,1} & R_{71,2} & \cdots & R_{71,2849} & R_{71,2850} \\ R_{72,1} & R_{72,2} & \cdots & R_{72,2849} & R_{72,2850} \end{bmatrix}$$

In some embodiments, the matrix can be used to precisely determine whether a match exists with respect to a particular physiological state and generate a flag within the user profile matrix. This flag can be used as an index for mapping a corresponding one or more IoT device settings to be adjusted in alignment with a preferred physiological state. In the alternative, the system can generate a report of user biomarker responses corresponding to a respective physiological state. In some embodiments, the system can generate an evolving model IoT device setting matrix, wherein the dynamic IoT device setting module 210 continuously learns the user's biomarker response to one or more IoT device settings; and thereby, adjusts the parameters of the user profile matrix using comparisons of the existing user profile matrix with a projected next set of matrix parameters. In some embodiments, dynamic IoT device setting module 210 may use principle component analysis (PCA) to determine the change and difference between the existing model and new user biomarker responses (to be described in more detail with reference to FIG. 4). In some embodiments, the dynamic IoT device setting module 210 may use neural network analysis to detect a shift in the user's biomarker response. If such a difference is repeatable, the dynamic IoT device setting module 210 will add the new set of data to the existing model.

It is appreciated that the components of exemplary operating environment 100 are exemplary and more or fewer components may be present in various configurations. It is appreciated that operating environment may be part of a distributed computing environment, a cloud computing environment, a client server environment, and the like.

In other words, as would be apparent to one of ordinary skill in the art after reading this description, the various features and functionality described herein may be implemented in the computing device architecture using any arrangement components necessary to perform the dynamic biometric regulation and control features (and functionality); and can be implemented in one or more separate or shared modules in various combinations and permutations.

As used herein, the terms agent and module might describe a given unit of functionality that can be performed in accordance with one or more embodiments of the present invention. As used herein, an agent or module might be implemented utilizing any form of hardware, software, or a combination thereof. For example, one or more processors, controllers, ASICs, PLAs, PALs, CPLDs, FPGAs, logical components, software routines or other mechanisms might be implemented to make up the agent or module. In implementation, the various agents and modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared agents or modules in various combinations and permutations. Even though various features or elements of functionality may be individually described or claimed as separate agents and modules, one of ordinary skill in the art will understand that these features and functionality can be shared among one or more common software and hardware elements, and such description shall not require or imply that separate hardware or software components are used to implement such features or functionality.

Figure 2:
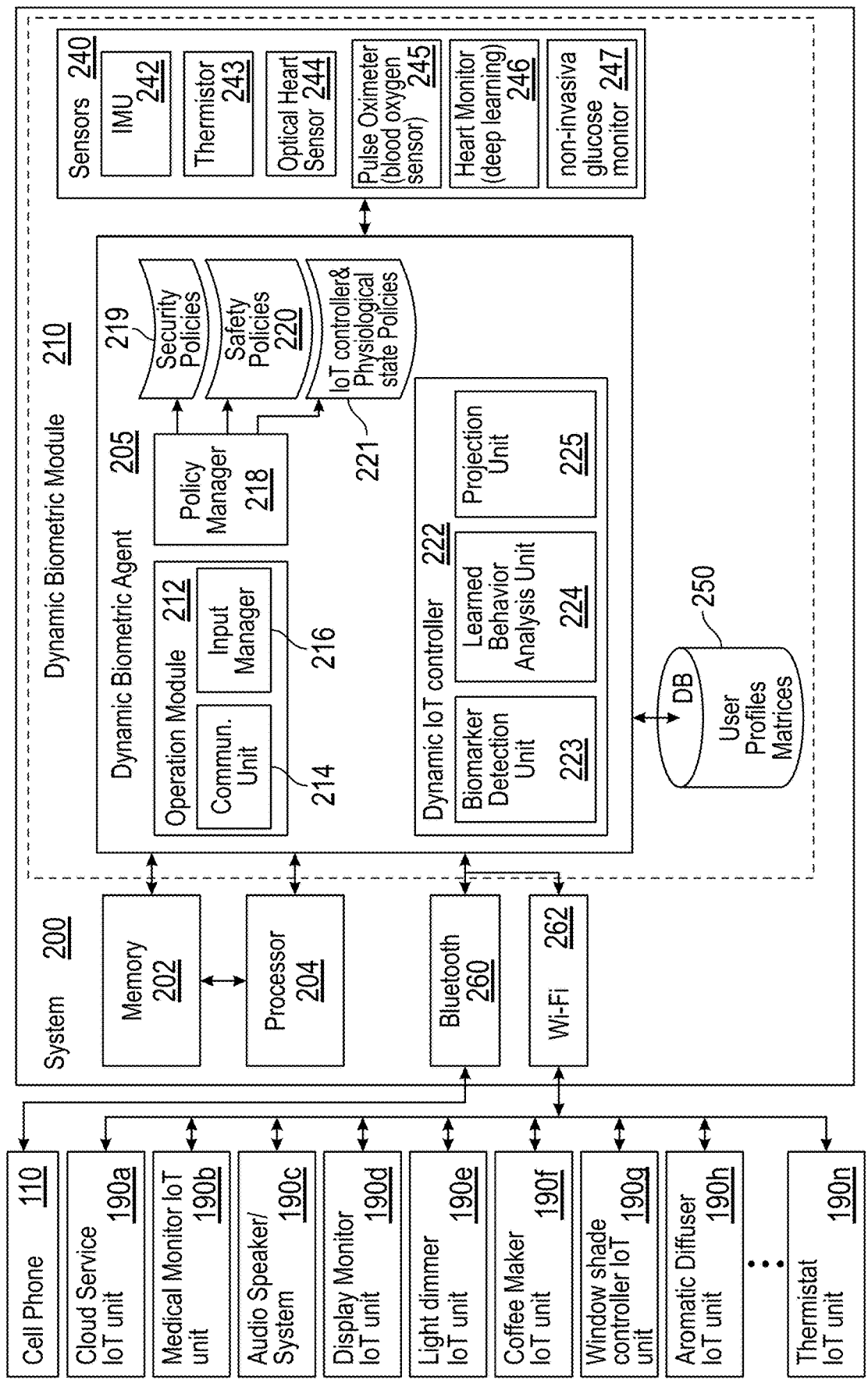
FIG. 2 is a block diagram of an exemplary system included within the client node of dynamic biometric regulation and control within a wearable client node of the exemplary network of FIG. 1, in accordance with some embodiments.

Referring now to FIG. 2, a block diagram of an exemplary system for dynamic biometric regulation and control within a biometric detection band of the exemplary network of FIG. 1, in accordance with some embodiments is presented. Exemplary system 200 may be implemented in a variety of ways. For example, all or a portion of exemplary system 200 may represent portions of exemplary network 100 in FIG. 1. As illustrated in FIG. 1, exemplary system 200 may include a memory 202, a processor 204, and a dynamic biometric module 210 having a storage database 250 for storing user for performing one or more tasks. For example, and as will be explained in greater detail below, dynamic biometric agent 205 may include an operations module 212; a policy manager 218 with associated security policies 219, safety policies 220, IoT controller and physiological state policies 221; and a dynamic IoT controller 222. The operations module 212 can include a communications unit 214 for generating communication signals to receive and transport user biomarker data. The operations module 212 can further include an input manager 216 for receiving user input regarding the first physiological state and the second physiological from a display unit (not shown). The policy manager 218 in collaboration with a user profile matrix may select safety standards from the safety policies 220 that align with the user's medical/psychological prognosis (i.e. a safety policy for a senior, a person experiencing anxiety disorder, a manic depressive personality, a person with Attention Deficit Disorder (ADD), and the like). Further, the policy manager 218 may select security rules from the security policies 219 for the purpose of protecting the privacy of each user's medical records based upon the user's profile matrix and the latest revision of the Health Insurance Portability and Accountability Act (HIPAA) laws, which mandate that organizations working with Protected Health Information (PHI) implement technical, physical, and administrative safeguards to protect sensitive information. Further, the policy manager 218 may select physiological state rules from the physiological state policies 219 for the purpose selecting the model user biomarker responses relating to the user's medical/psychological prognosis (i.e. a transitional state policy for a person experiencing stress, a person experiencing anxiety disorder, a manic depressive personality, a person with Attention Deficit Disorder (ADD), and the like).

In some embodiments, the dynamic IoT controller 222 may include a biomarker detection unit 223, a learned behavior analysis unit 224, and a projection unit 225. The biomarker detection unit 223 in some implementations can detect whether the user biomarker response aligns with a first physiological state and a second physical physiological state. The learned behavior analysis unit 224 can make a determination as to the similarities between the monitored user biomarker response data and the data found in the user's profile matrix using a learning algorithm that detects which patterns repeat in alignment with either the first psychological state or the second psychological state. The projection unit 225 can use the output of the learned behavior analysis unit 224 to conduct predictive analysis, projecting one or more IoT device settings based upon this input.

In cooperation with the dynamic biometric agent 205, the system 200 may include a sensor unit 240 having one or more of the following sensors: IMU 242, thermistor 243, optical heart sensor 244, pulse oximeter (blood oxygen sensor) 245, heart monitor (deep learning) 246, and non-invasive glucose monitor 247. The system 200 can also include one or more of the various communication utilities: Bluetooth 260, Wi-Fi 262, NFC 264, RFID 266, and GSM 268. Further, the system 200 can exchange information with other client nodes 105.

There are a great variety of IoT devices (190a-n) that may be coupled to the dynamic biometric module 210 using the Bluetooth communication mechanism 260 or Wi-Fi 262. For example the dynamic biometric module 210 may couple to a cloud service 190a for activating a store and back up service during the period when the user may be experiencing a particular physiological state. A medical monitor 190b may be connected to the dynamic biometric module 210 for the purpose of facilitating communication between a physician and/or a psychologist and the user during a particular physiological state. Additionally, an audio speaker system 190c may be connected to the dynamic biometric module 210 for the purpose of playing an affirmation or music that places the user in the physiological preferred state. A display monitor 190d may be connected to the dynamic biometric module 210 for the purpose of changing a visual display so that the user can be added in transitioning to a physiological state that is more desirable. Adjusting a light dimmer 190e or a window shade controller 190g may also help to transition the user into the preferred psychological and physiological state. Adjusting the sensory perception of smell can also transition the user into a preferred physiological state, such as turning on a coffee maker 190f or turning on an aromatic diffuser 190h. Further, a thermostat 190n may be connected to the dynamic biometric module 210 for the purpose of transitioning to use it to a preferred physiological state.

In operation, the processor 204 in collaboration with the policy manager 218 may communicate with the network 150 to initiate a safety protocol of the safety policies 220 that ensures the safety of the user based upon the user's medical condition. Further, the processor 204 in collaboration with the policy manager 218 may initiate a security protocol 219 for the purpose of protecting the privacy of each user's medical records prior to retrieval of user profile data. For example, multiple security levels of tiered remote monitoring with data-dissemination can be provided to healthcare servers, maximizing allocation and safety protocols. In particular, the processor 204 in collaboration with the operation module 212 may retrieve the user profile matrix from a local storage unit 250. Next, the processor 204 in collaboration with the Further, the biomarker detection unit 223 may detect the biomarkers of the user using the various sensors (243, 244, 245, 246, and 247) of the sensing unit 240. For example, in some embodiments the processor 204 in collaboration with the biomarker detection unit 223 may retrieve one or more to the following: the user's temperature from a thermistor 243; the user's blood pressure from a sensing unit having a deep learning algorithm associated with monitoring heart rate; the user's blood oxygen level from a pulse oximeter blood oxygen sensor 245; the user's blood glucose level from a non-invasive glucose monitor 247; and/or the user's pulse from an optical heart sensor 244. In some embodiments, the biomarker detection unit 223 may retrieve user input, including keyboard data input or voice input relating to psychological data, such as any data relating to their emotional or physical state.

Moreover, the learned behavior analysis unit 224 may detect a pattern in the user biomarker data within the user profile matrix. For example, the learned behavior analysis unit 224 may monitor the user biomarker response to various IoT device settings as it pertains to various physiological states using advanced machine-learning algorithms, including principal component analysis and neural network computations. Moreover, based upon the detected physiological state, the sensed biomarkers, IoT controller and physiological state policies 221, and the user profile matrix, the learned behavior analysis unit 224 in collaboration with the policy manager 218 may be operable to detect a pattern. In particular, the learned behavior analysis unit 224 can use the aforementioned data to build an active profile model of user's biomarker response to IoT device settings. Such a model includes intertwined array of the users' measure of central tendency biomarker indications, user's physiological state data, time parameters, and the like. The parameters of the model can be stored in a matrix of a local database of the dynamic biometric module 210, wherein multiple dimensions can be stored.

In some embodiments, the matrix can be used to precisely determine whether a match exists with respect to a particular physiological state and generate a flag within the user profile matrix. This flag can be used as an index for mapping a corresponding one or more IoT device settings to be adjusted in alignment with a preferred physiological state. In the alternative, the system can generate a report of user biomarker responses corresponding to a respective physiological state. In some embodiments, the system can generate an evolving model IoT device setting matrix, wherein the learned behavior analysis unit 224 continuously learns the user's biomarker response to one or more IoT device settings; and thereby, adjusts the parameters of the user profile matrix using comparisons of the existing user profile matrix with a projected next set of matrix parameters. In some embodiments, learned behavior analysis unit 224 may use principle component analysis (PCA) to determine the change and difference between the existing model and new user biomarker responses (to be described in more detail with reference to FIG. 4). In some embodiments, the learned behavior analysis unit 224 may use neural network analysis to detect a shift in the user's biomarker response. If such a difference is repeatable, the learned behavior analysis unit 224 will add the new set of data to the existing model.

In some embodiments, the output of the learned behavior analysis unit 224 can be fed into the projection unit 225, which can predict one or more IoT device settings in alignment with a preferred physiological state based upon the IoT controller and physiological state policies 221. In particular, the projection unit 225 can use the data associated with the repetitive user biomarker responses as an index to select one or more IoT device settings in alignment with a preferred physiological state. That is, the projection unit 225 can use the input from the learned behavior analysis unit 224 to perform a type of predictive analysis, generating highly probable IoT device settings that can aid in transitioning the user into the preferred physiological state.

Figure 3:
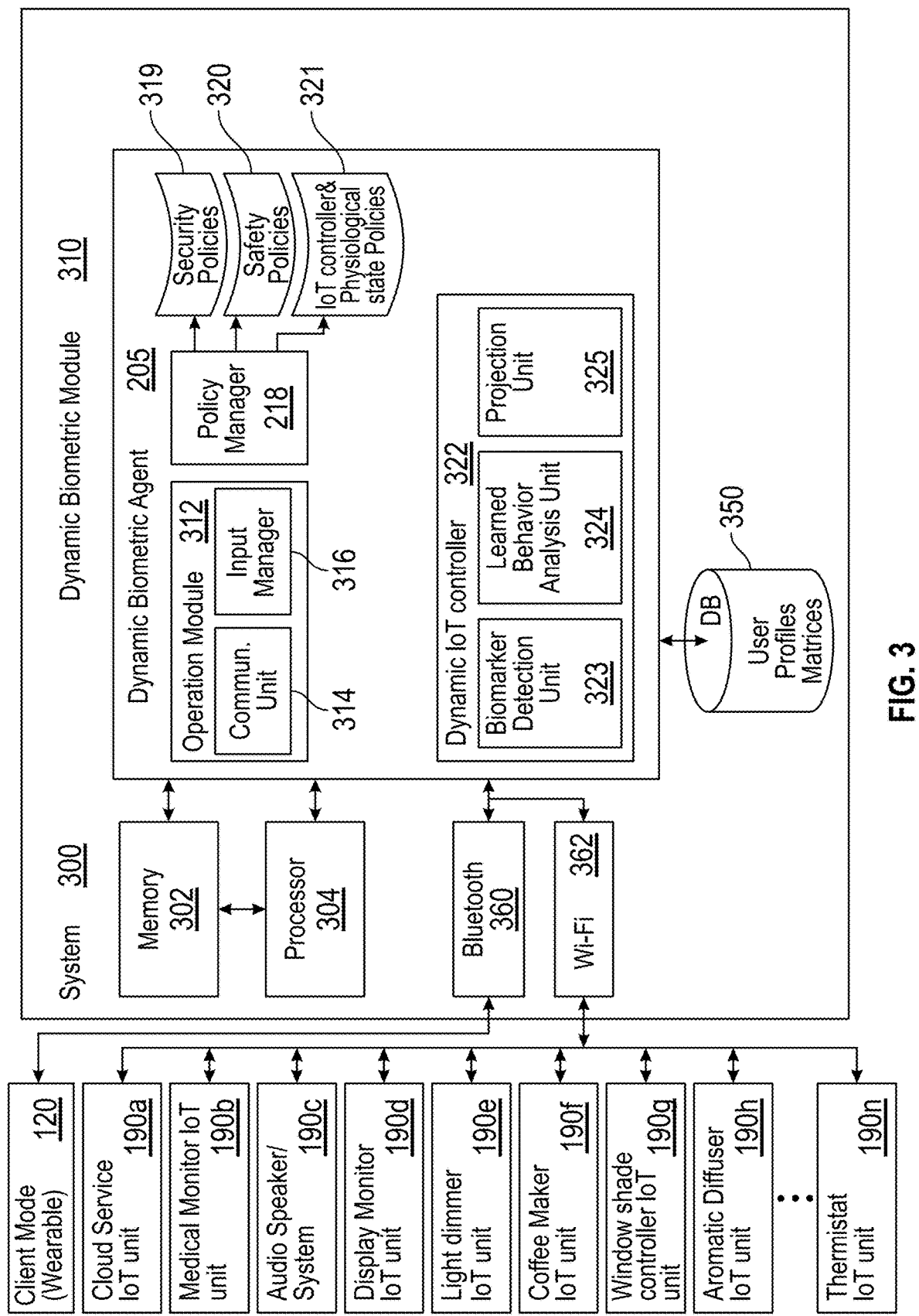
FIG. 3 is a block diagram of a system included within the client node device or server of dynamic biometric regulation and control within a mobile device and server of the exemplary network of FIG. 1, in accordance with some embodiments.

Referring now to FIG. 3, a block diagram of another system 300 for dynamic biometric regulation and control within a computing device and server of the exemplary network of FIG. 1, in accordance with some embodiments is illustrated. Similar to the system 200, system 300 may include memory 302, processor 304, dynamic biometric agent 310, local database 350, Bluetooth 360 and Wi-Fi 362. The dynamic biometric agent 310 differs from the dynamic biometric module 210 of FIG. 2 in that it does not include a sensor unit such as unit 240 disclosed in FIG. 2. Dynamic biometric agent 310 may include an operations module 312; a policy manager 318 with associated security policies 319, safety policies 320, IoT controller and physiological state policies 321; and a dynamic IoT controller 322. The dynamic IoT controller 322 may include a biomarker detection unit 323, a learned behavior analysis unit 324, and a projection unit 325. The biomarker detection unit 323 in some implementations can detect whether the user biomarker response aligns with a first physiological state and a second physical physiological state. Further, similar to system 200, system 300 may include an interface for communication with a cloud service 190a and various array of IoT devices: medical monitor 190b, audio system/speaker 190c, display monitor 190b, light dimmer switch 190e, coffee maker 190f, window shade controller 190g, an aromatic diffuser 190h, and thermostat 190n (as shown in FIG. 3).

In operation, system 300 may exchange data with system 200 in an effort to detect user biomarker response patterns. As noted supra, the various agents (205, 310) and modules 210 described herein can be implemented as discrete modules or the functions and features described can be shared in part or in total among one or more modules or agents. In other words, as would be apparent to one of ordinary skill in the art after reading this description, the various features and functionality described herein may be implemented in any given application and can be implemented in one or more separate or shared agents or modules in various combinations and permutations. Even though various features or elements of functionality may be individually described or claimed as separate agents and modules, one of ordinary skill in the art will understand that these features and functionality can be shared among one or more common software and hardware elements, and such description shall not require or imply that separate hardware or software components are used to implement such features or functionality.

Figure 4:
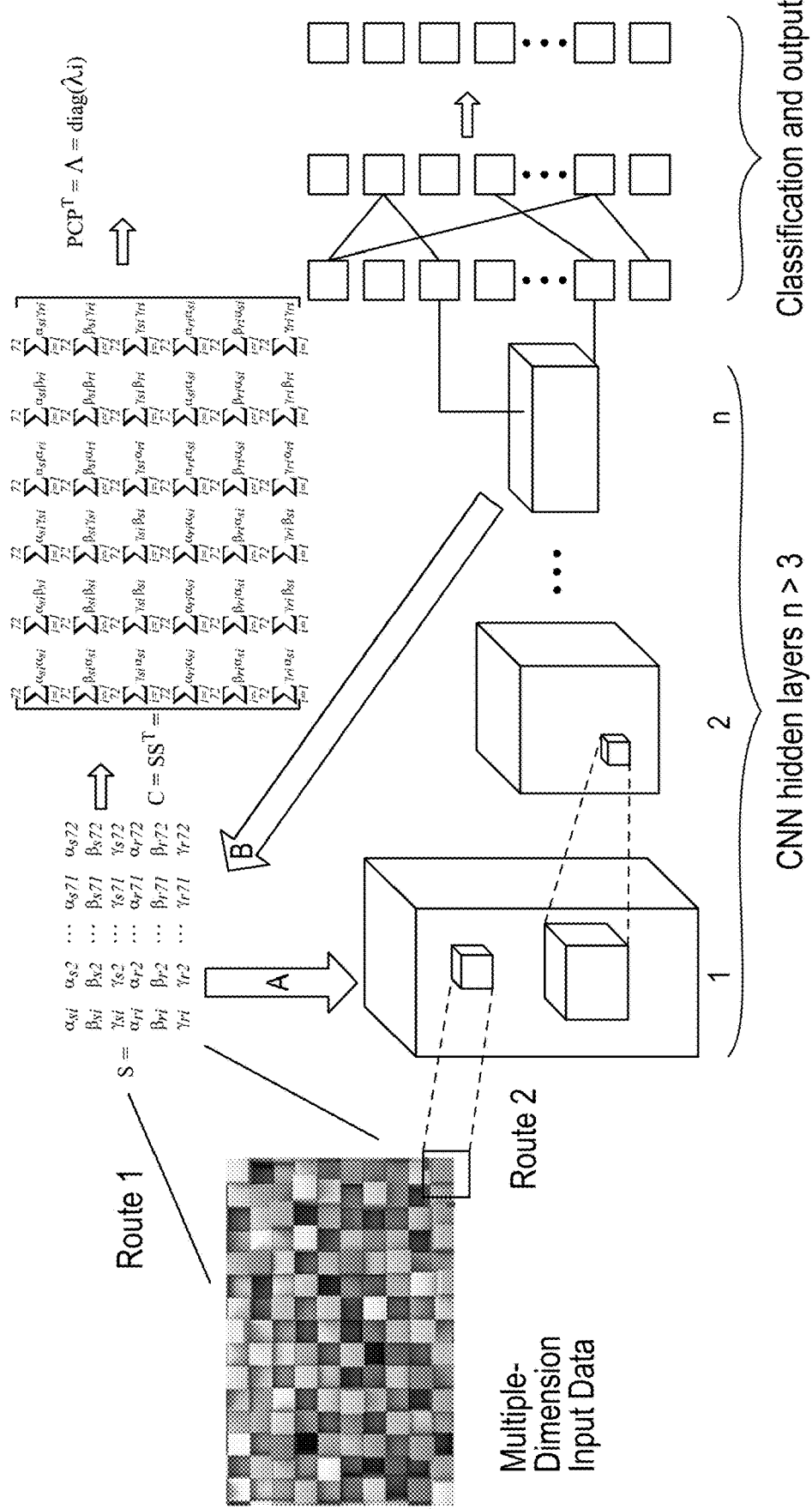
FIG. 4 is a block diagram of an enhanced machine-learning algorithm for identifying repetitive actions within the user's biomarker response used by the Dynamic IoT controller FIGS. 2 and 3 of the dynamic biometric agent, in accordance with some embodiments.

Referring now to FIG. 4, a block diagram of an enhanced machine-learning algorithm for identifying repetitive patterns within the user's biomarker response to differing IoT devices and device settings in an effort to identify repetitive patterns associated with each predefined physiological state, in accordance with some embodiments is shown. In particular, this novel technique can be implemented within the learned behavior analysis unit (224, 324) of FIGS. 2 and 3 within the dynamic biometric agents (205, 310). As noted supra, the system and method of dynamic biometric regulation and control may detect and record a comprehensive set of user biomarker response to differing IoT devices and device settings. In particular, real-time body status (heartbeat, blood oxygen level, blood pressure), and time (time and time periods of aforementioned activities) can be detected or received from the user as input and stored within the user profile matrix. Further, the user may use the keyboard of the mobile device (110, 120) to enter the emotional state, by either selecting a numerical value or entering words associated with their psychological state (e.g. a number from "0" (least) to "10" (best); or "euphoric").

As shown in FIG. 4, the data can be constructed as multiple-dimension matrices of data. In some embodiments, one of the two routes (Route 1 or Route 2) can be used to process the data and identify various physiological/psychological states of the user. Particularly, S represents the matrix of features extracted from the multiple-dimension input data (shown below and in FIG. 4).

$$S = \begin{bmatrix} \alpha_{s,1} & \alpha_{s,2} & \cdots & \alpha_{s,71} & \alpha_{s,72} \\ \beta_{s,1} & \beta_{s,2} & \cdots & \beta_{s,71} & \beta_{s,72} \\ \vdots & \vdots & \ddots & \vdots & \vdots \\ \beta_{r,1} & \beta_{r,2} & \cdots & \beta_{r,71} & \beta_{r,72} \\ \gamma_{r,1} & \gamma_{r,2} & \cdots & \gamma_{r,71} & \gamma_{r,72} \end{bmatrix}$$

The variables, $\alpha$, $\beta$, and $\gamma$, represent a typical feature at a different time sampling sequence (s) or recovering sequence (r). Matrix Ce is derived from the multiplication of matrix S with its rotating matrix along the diagonal direction ($S^T$). As shown in FIG. 4, matrix C is derived from the equation $C=SS^T$ shown in FIG. 4:

$$C = \begin{bmatrix} \sum_{i=1}^{72} \alpha_{si}\alpha_{si} & \sum_{i=1}^{72} \alpha_{si}\beta_{si} & \cdots & \sum_{i=1}^{72} \alpha_{si}\beta_{ri} & \sum_{i=1}^{72} \alpha_{si}\gamma_{ri} \\ \sum_{i=1}^{72} \beta_{si}\alpha_{si} & \sum_{i=1}^{72} \beta_{si}\beta_{si} & \cdots & \sum_{i=1}^{72} \beta_{si}\beta_{ri} & \sum_{i=1}^{72} \beta_{si}\gamma_{ri} \\ \vdots & \vdots & \ddots & \vdots & \vdots \\ \sum_{i=1}^{72} \beta_{ri}\alpha_{si} & \sum_{i=1}^{72} \beta_{ri}\beta_{si} & \cdots & \sum_{i=1}^{72} \beta_{ri}\beta_{ri} & \sum_{i=1}^{72} \beta_{ri}\gamma_{ri} \\ \sum_{i=1}^{72} \gamma_{ri}\alpha_{si} & \sum_{i=1}^{72} \gamma_{ri}\beta_{si} & \cdots & \sum_{i=1}^{72} \gamma_{ri}\beta_{ri} & \sum_{i=1}^{72} \gamma_{ri}\gamma_{ri} \end{bmatrix}$$

Matrix P is derived from the diagonalization of matrix Ce. That is, matrix C is a known symmetric covariance matrix consisting of the input data. P is a transformation matrix to be derived while pursuing a diagonalization of C into matrix Λ. Matrix Λ is the diagonal matrix of eigenvalues λ associated with matrix C, where the set of eigenvalues, {λ}, contains the principal components. As indicated in FIG. 4, matrix $\Lambda=PCP^T=\text{diag}(\lambda_i)$. Variable n represents the number of hidden layers of the CNN model.

In operation during Route 1, the data can be examined and a set of features can be extracted using one or more linear, polynomial, or exponential formulas to form matrices with less dimensions. In some embodiments, the size of data can be shrunk to 1/10 of the original data. Next, the extracted feature matrices can be processed by manipulation of the data and pattern recognition. In particular, some embodiments may employ the use of the modified principal component analysis (PCA) and Linear Discriminant Analysis (LDA) of linear algebra, to identify user biomarker response in alignment with each physiological and psychological state. In contrast, the operation during the route 2 may include directly processing the original data using a machine learning technique, such as employing the use of a convolutional neural network (CNN). From this type of analysis, the classification and identification of possible IoT device settings having a higher probability of transitioning the user into a preferred physiological state.

Beneficially, the Route 1 method has the advantage of computation efficiency and fast processing speed. The disadvantage, however, is that the method of Route 1 can be of relatively low precision. In contrast, the method of Route 2 can be quite precise but may require a large amount of computation resources (CPU time and memory cells) and consume a much longer computation time.

In some embodiments, the system and method for dynamic biometric regulation and control uses an enhanced algorithm whereby two connections (A and B) are made between Route 1 and 2 to significantly improve the accuracy and computation efficiency, creating a hybrid solution. In particular with reference to route A, a set of comprehensive features can be extracted as the input data for machine learning using neural network computation analysis. Since the feature input data is much smaller in size than the original data, the machine learning computation will be much faster and consume less computation resources, while the accuracy is maintained. During route B, the original data can be processed using machine-learning, such as CNN to extract a set of more representative features and related weight factors. These extracted features will be more precise and comprehensive then the features extracted by a set of fixed formulas. Accordingly, these extracted data can then be used as input data for PCA or LDA matrix manipulation in an effort to identify and classify the users' physiological state.

Figure 5A:
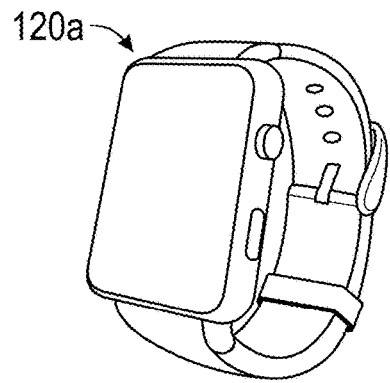
FIG. 5A is a perspective view of the front of a wristband of the exemplary network of FIG. 1, in accordance with some embodiments.
Figure 5B:
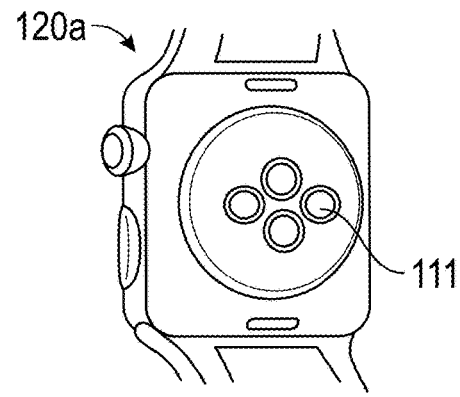
FIG. 5B is a perspective view of sensors of the back of the wristband of the exemplary network of FIG. 1, in accordance with some embodiments.

Referring now to FIG. 5A, a perspective view of the front of a wristband 120a of the exemplary network of FIG. 1, in accordance with some embodiments is shown. The wristband (D-Band™) is a wearable monitoring device, having system 200 of FIG. 2, that is worn on the wrist, where the user's heart rate (pulse), blood pressure, blood glucose level, temperature, and blood oxygen are precisely monitored and measured. As shown in FIG. 5B, a perspective view of the back of the wristband 120a of the exemplary network of FIG. 1, illustrates that various sensors can be embedded into the wristband 120a. These may include various types of sensors in direct and indirect contact with the user; including, IMU 242, thermistor 243, optical heart sensor 244, pulse oximeter (blood oxygen sensor) 245, heart monitor (deep learning) 246, non-invasive glucose monitor 247, and the like. The system 200 within the wristband 120a can include one or more of the various communication utilities, including Bluetooth, Wi-Fi, NFC, RFID, GSM, and the like. Further, the system 200 within the waistband 120a can exchange information with other client nodes (105, 145).

Figure 5C:
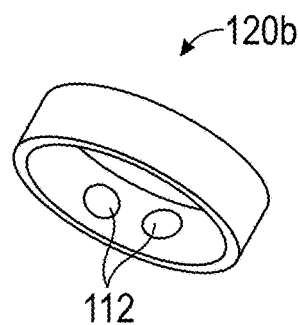
FIG. 5C is a perspective view of a ring of the exemplary network of FIG. 1, in accordance with some embodiments.

Referring now to FIG. 5C, a perspective view of a ring 120b of the exemplary network of FIG. 1, in accordance with some embodiments, is displayed. The ring 120b is a wearable monitoring device, having system 200 of FIG. 2, that is worn on the finger where the user's heart rate (pulse), blood pressure, blood glucose level, temperature, and blood oxygen are precisely monitored and measured. Similar to the wristband 120a, the ring 120b includes system 200 of FIG. 2. In particular, the band 120b may be in the form of a ring (D-Ring™) to be worn around the user's finger, serving as a wearable monitoring device that works in concert with the wristband and within an established healthcare network. In particular, key biomarkers can be monitored and communicated within the network through the use of the ring. Similarly, ring 120b may include various types of sensors 112, representing one or more of the various sensors to the IMU 242, thermistor 243, optical heart sensor 244, pulse oximeter (blood oxygen sensor) 245, heart monitor (deep learning) 246, and non-invasive glucose monitor 247 shown in FIG. 2. The system 200 within the ring 110b can include one or more of the various communication utilities, including Bluetooth, Wi-Fi, NFC, RFID, GSM, and the like. Further, the system 200 within the ring 110b can exchange information with other client nodes (105, 145).

Figure 5D:
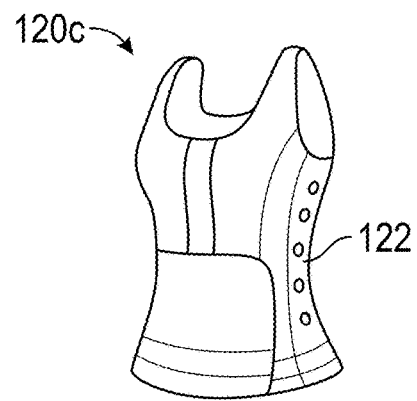
FIG. 5D is a perspective view of the front of a vest of the exemplary network of FIG. 1, in accordance with some embodiments.
Figure 5E:
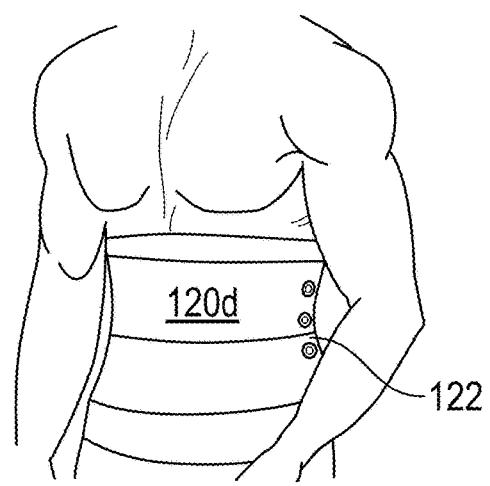
FIG. 5E is a perspective view of the waistband of the exemplary network of FIG. 1, in accordance with some embodiments.

Referring now to FIGS. 5D and 5E, a perspective view of a vest 120c and waistband 120d of the exemplary network of FIG. 1, in accordance with some embodiments is illustrated. The vest 120a may include a wearable monitoring device (including system 200 of FIG. 2) that is worn on the torso where the user's biomarker responses are precisely monitored and measured. Likened unto the wristband 120a, both the vest 120a and the waistband 120d may include the system 200 as indicated in FIGS. 1 and 2. One or more sensors 122 (240) may be embedded with the vest 120a as shown. In particular, these sensors 122 can represent one or more of the various types of sensors, IMU 242, thermistor 243, optical heart sensor 244, pulse oximeter (blood oxygen sensor) 245, heart monitor (deep learning) 246, and non-invasive glucose monitor 247 of FIG. 2. The system 200 within the vest 120a and the waistband 120d can include one or more of the various communication utilities, including Bluetooth, Wi-Fi, NFC, RFID, GSM, and the like. Further, the system 200 within the vest 120a and the waistband 120d can exchange information with other client nodes (105, 145).

Referring now to FIG. 6A, an exemplary flow diagram of a method for dynamic biometric regulation and control, in accordance with some embodiments is shown. In an action 605, the method may include calibrating a dynamic IoT device setting module with user biomarker response to one or more IoT device settings. For example, the calibrating step of the method may include receiving user input defining the first physiological state and the second physiological state. Further, the calibrating step of the method may include retrieving a first set of model biomarkers associated with the first physiological state and a second set of model biomarkers associated with the second physiological state from a model database. Additionally, the calibrating step of the method may include retrieving one or more IoT device settings associated with the first physiological state and with the second physiological state from a model database. Further, the calibrating step of the method may include storing user input, the first set of model biomarkers, the second set of model biomarkers, and the retrieved IoT device settings in the user profile matrix. Moreover, the calibrating step of the method may include adjusting one or more IoT device settings to the retrieved one or more IoT device settings associated with the second physiological state. As feedback, the calibrating step of the method may include monitoring user biomarker response to the adjusted one or more IoT device settings.

In an action 610, the method may include monitoring one or more user biomarkers using the dynamic IoT device setting module. For example, the monitoring step of the method may include retrieving the user's temperature from a thermistor; retrieving the user's blood pressure from a heart rate sensing unit having a deep learning algorithm; retrieving the user's blood oxygen level from a pulse oximeter blood oxygen sensor; retrieving the user's pulse from an optical heart sensor; retrieving the user's blood glucose levels from a non-invasive glucose monitor; and repeating the retrieving until a stop command is issued. Further, in an action 615, the method may include storing the one or more user biomarkers in a user profile matrix.

Further, the method may include detecting a first physiological state based upon the user profile matrix in an action 620. For example, the detecting step of the method may include retrieving a first set of model biomarkers associated with the first physiological state from the user profile matrix. Further, the detecting step of the method may include comparing the monitored one or more user biomarkers with the first set of model biomarkers. Next, the detecting step of the method may include detecting a match of the monitored one or more user biomarkers with the first set of model biomarkers and setting a first flag, when the match occurs.

In a decision action 625, the method may include determining if the sensed user biomarkers align with the first physiological state. For example, the decision action may include checking to see if the first flag is set, indicating the existence of the first physiological state. In response, the method may include adjusting, in response to the existence of the first physiological state, one or more IoT device settings associated with a second physiological state in an action 630. For example, the adjusting step of the method may include retrieving the one or more IoT device settings associated with the second physiological state from the user profile matrix and modifying the setting of the one or more IoT devices to match the retrieved one or more IoT device settings. For example, modifying the setting may comprise adjusting a thermostat to align with one or more temperature settings of the second physiological state from the user profile matrix. In some embodiments, modifying the setting may include changing a displayed image on an electronic surface to align with the second physiological state. The modifying step may also include changing a broadcasted audio or broadcasted video to align with the second physiological state. Further, the modifying step of the may include adjusting a light switch dimmer, window shade control, or an aromatic diffuser to align with the second physiological state. Finally, the modifying step of the method may include updating the user profile matrix with these adjusted settings.

In an action 635, the method may include sensing user biomarker response to the adjusted settings. Further in a decision action 640, the method may include determining if the sensed user biomarkers align with the second physiological state. For example, the determining step of the method may include retrieving a second set of model biomarkers associated with the second physiological state from the user profile matrix. Further, the determining step of the method may include comparing the sensed user biomarker response with the second set of model biomarkers. Next, the determining step of the method may include detecting a match of the sensed user biomarker response with the second set of model biomarkers. Further, the determining step of the method may include setting a second flag, when the match occurs.

In an action 650, the method may include adjusting, in response to nonalignment of the sensed biomarkers with the second physiological state, the one or more IoT devices based upon a learning algorithm (having the user profile matric and optional clinician input), until alignment of the sensed biomarkers with the second physiological state occurs. For example, the adjusting based upon the learning algorithm step of the method may include retrieving a model set of user biomarker responses associated with the second physiological state from a datastore. Next, the adjusting step of the method may include extracting a set of one or more abridged matrices from the user profile matrix. Further, the adjusting step of the method may include selecting a first matrix from the extracted set. Additionally, the adjusting step of the method may include processing the first matrix using a Convolution Neural Network (CNN). Next, the adjusting step of the method may include extracting a second matrix from the CNN processed matrix. Further, the adjusting step of the method may include detecting the similarity between the second matrix and the retrieved model set of user biomarker responses using a pattern recognition technique, such as Principal Component Analysis (PCA) or Linear Discriminate Analysis (LDA). Moreover, the adjusting step of the method may include projecting a next set of one or more IoT device settings based upon the similarity and modifying the one or more IoT devices settings to match the next set. In some embodiments, the projected next set of one or more IoT device settings may be based upon clinician input. For verification purposes, the adjusting step of the method may include sensing user biomarker response to the modified IoT device settings and determining if the sensed user biomarkers align with the model set of user biomarker responses. This process of adjusting can be repeated, wherein the projecting, modifying, sensing, and determining step until sensed user biomarkers align with the second physiological state.

Referring now to FIG. 6B, an exemplary flow diagram of a method for monitoring user biomarker response to IoT device settings using an enhanced machine-learning algorithm to identify repetitive actions in user biomarker response of FIG. 6A (step 650) in accordance with some embodiments is shown. In particular, the user data may be retrieved in an action 652. Next a master matrix may be formed in an action 654. As described with reference to FIG. 3, there are three routes (Route 1, Route 2, or the Enhanced Route AB) that the data can take in order to be processed. In particular, the switches S1-S4 can be set to enable a first mode through Route 1; a second mode through Route 2; and third mode through the Enhanced Route AB. As shown in FIGS. 4 and 6B, asymmetric dual-path processing can occur within the learned behavior analysis unit (224, 324 of FIGS. 2 and 3), having a set of switches (S1-S4) for enabling a first mode of operation through a first route, a second mode of operation through a second route, and a third mode of operation through a hybrid route (wherein the hybrid route is associated with both the first route and the second route). In some embodiments, the mode of operation may be set by the manufacturer of the dynamic biometric module (210, 310), wherein switches S1-S4 are opened and/or closed to define how the data is processed within the learned behavior analysis unit (224, 324) of the dynamic IoT controller (222, 322). In some examples, an administrator of the system (200, 300) can set which mode of operation is preferred. Accordingly, the administrator can select which mode of operation will be used to transition the user from a current state to a desired state. For example, during the first mode of operation having the first route (Route 1), one or more abridged matrices may be generated using the master matrix in an action 656. During this first mode of operation, switches S1 and S4 are open, while switches S2 and S3 remain closed. Since switch S3 is closed and switch S4 is open, the data processing proceeds to the next step of action 664. Particularly, Next in an action 664, the one or more matrices can be processed using one or more pattern recognition techniques [e.g. Principal Component Analysis (PCA), Linear Discriminant Analysis (LDA)] to generate an output (Output$_{R1}$) for enabling the projection unit (225, 325) to select IoT settings associated with shifting the user to a desired physiological state using predictive analysis (as noted supra with respect to FIGS. 2 and 3).

In some embodiments, the system (200, 300) and method may be set to process the data using Route 2, wherein the data is processed using a Convolution Neural Network (CNN) as indicated in action 650. In one example, the administrator may set switches S1 and S4 closed, while switches S2 and S3 are open. Therein, the data will be processed the learned behavior analysis unit (224, 324) of the dynamic IoT controller (222, 322) through Route 2 after step 644. Particularly, the data will be processed using CNN in an action 660 to directly produce an output for the second route (Output$_{R2}$) to be fed into the projection unit (225, 325). In the third mode of operation, the system (200, 300) and method may be set to process the data using the hybrid Route AB, wherein the data is processed using both CNN and pattern recognition techniques, such as PCA and LDA. In particular as indicated in action 650, the system and method may be set to process the matrix using the Enhanced Route AB, wherein one abridged matrix can be extracted from the set of one or more abridged matrices in an action 658. In particular, the administrator may set switches S1 open and S2 closed, while switches S3 is open to steer the data towards action 662 where a set of features and relative weight factors are extracted and switch S4 is set to steer data to be processed using PCA or LDA in action 664. More particularly, one abridged matrix can be sent to be process using CNN in the action 660. Further, a matrix can be extracted from the CNN processed matrix that includes a set of features and relative weight factors in an action 662. In the action 664, the extracted matrix can be processed using one or more pattern recognition techniques [e.g. Principal Component Analysis (PCA), Linear Discriminant Analysis (LDA)] to generate an output (Output$_{Rmod}$) for enabling the projection unit (225, 325) to generate the associated IoT settings. Accordingly, the Enhanced Route AB of processing the data can generate an optimum result, having precision, and speed, without the excessive use of computing resources.

It should be appreciated that the methods described herein may be performed with a digital processing system, such as a conventional, general-purpose computer system. Special purpose computers, which are designed or programmed to perform only one function may be used in the alternative. FIG. 7 is an illustration showing an exemplary computing device, which may implement the embodiments described herein. The computing device of FIG. 6 may be used to perform embodiments of the functionality for performing the dynamic biometric regulation and control in accordance with some embodiments (as outlined in FIGS. 6A and 6B). The computing device includes a central processing unit (CPU) 702, which is coupled through a bus 706 to a memory 704, and mass storage device 708. Mass storage device 708 represents a persistent data storage device such as a floppy disc drive or a fixed disc drive, which may be local or remote in some embodiments. The mass storage device 708 could implement a backup storage, in some embodiments. Memory 704 may include read only memory, random access memory, and the like. Applications resident on the computing device may be stored on or accessed through a computer readable medium such as memory 704 or mass storage device 708 in some embodiments. Applications may also be in the form of modulated electronic signals modulated accessed through a network modem or other network interface of the computing device. It should be appreciated that CPU 702 may be embodied in a general-purpose processor, a special purpose processor, or a specially programmed logic device in some embodiments.

Display 712 is in communication with CPU 702, memory 704, and mass storage device 708, through bus 706. Display 712 is configured to display any visualization tools or reports associated with the system described herein. Input/output device 710 is coupled to bus 706 in order to communicate information in command selections to CPU 702. It should be appreciated that data to and from external devices may be communicated through the input/output device 710. CPU 702 can be defined to execute the functionality described herein to enable the functionality described with reference to FIGS. 1-6B. The code embodying this functionality may be stored within memory 704 or mass storage device 708 for execution by a processor such as CPU 702 in some embodiments. The operating system on the computing device may be iOS™, MS-WINDOWS™, OS/2™, UNIX™, LINUX™, or other known operating systems. It should be appreciated that the embodiments described herein may be integrated with virtualized computing system also.

The embodiments can also be embodied as computer readable code on a non-transitory computer readable medium. The computer readable medium is any data storage device that can store data, which can be thereafter read by a computer system. Examples of the computer readable medium include hard drives, network attached storage (NAS), read-only memory, random-access memory, CD-ROMs, CD-Rs, CD-RWs, magnetic tapes, flash memory devices, and other optical and non-optical data storage devices. The computer readable medium can also be distributed over a network coupled computer system so that the computer readable code is stored and executed in a distributed fashion. Embodiments described herein may be practiced with various computer system configurations including hand-held devices, tablets, microprocessor systems, microprocessor-based or programmable consumer electronics, minicomputers, mainframe computers and the like. The embodiments can also be practiced in distributed computing environments where tasks are performed by remote processing devices that are linked through a wire-based or wireless network.

In various embodiments, one or more portions of the methods and mechanisms described herein may form part of a cloud-computing environment. In such embodiments, resources may be provided over the Internet as services according to one or more various models. Such models may include Infrastructure as a Service (IaaS), Platform as a Service (PaaS), and Software as a Service (SaaS). In IaaS, computer infrastructure is delivered as a service. In such a case, the computing equipment is generally owned and operated by the service provider. In the PaaS model, software tools and underlying equipment used by developers to develop software solutions may be provided as a service and hosted by the service provider. SaaS typically includes a service provider licensing software as a service on demand. The service provider may host the software, or may deploy the software to a customer for a given period of time. Numerous combinations of the above models are possible and are contemplated.

In the above description, numerous details are set forth. It will be apparent, however, to one skilled in the art, that the present invention may be practiced without these specific details. In some instances, well-known structures and devices are shown in block diagram form, rather than in detail, in order to avoid obscuring the present invention.

It is to be understood that the above description is intended to be illustrative, and not restrictive. Many other embodiments will be apparent to those of skill in the art upon reading and understanding the above description. Although the present invention has been described with reference to specific exemplary embodiments, it will be recognized that the invention is not limited to the embodiments described, but can be practiced with modification and alteration within the spirit and scope of the appended claims. Specific functional details disclosed herein are merely representative for purposes of describing embodiments. Embodiments may, however, be embodied in many alternate forms and should not be construed as limited to only the embodiments set forth herein. Accordingly, the specification and drawings are to be regarded in an illustrative sense rather than a restrictive sense. The scope of the invention should, therefore, be determined with reference to the appended claims, along with the full scope of equivalents to which such claims are entitled.

Although the method operations were described in a specific order, it should be understood that other operations may be performed in between described operations, described operations may be adjusted so that they occur at slightly different times or the described operations may be distributed in a system which allows the occurrence of the processing operations at various intervals associated with the processing.

It should be understood that although the terms first, second, etc. may be used herein to describe various steps or calculations, these steps or calculations should not be limited by these terms. These terms are only used to distinguish one step or calculation from another. For example, a first calculation could be termed a second calculation, and, similarly, a second step could be termed a first step, without departing from the scope of this disclosure. As used herein, the term "and/or" and the "I" symbol includes any and all combinations of one or more of the associated listed items. As used herein, the singular forms "a", "an" and "the" are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. Therefore, the terminology used herein is for the purpose of describing particular embodiments only and is not intended to be limiting.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved. With the above embodiments in mind, it should be understood that the embodiments might employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing. Any of the operations described herein that form part of the embodiments are useful machine operations. The embodiments also relate to a device or an apparatus for performing these operations. The apparatus can be specially constructed for the required purpose, or the apparatus can be a general-purpose computer selectively activated or configured by a computer program stored in the computer. In particular, various general-purpose machines can be used with computer programs written in accordance with the teachings herein, or it may be more convenient to construct a more specialized apparatus to perform the required operations.

A module, an application, a layer, an agent or other method-operable entity could be implemented as hardware, firmware, or a processor executing software, or combinations thereof. It should be appreciated that, where a software-based embodiment is disclosed herein, the software can be embodied in a physical machine such as a controller. For example, a controller could include a first module and a second module. A controller could be configured to perform various actions, e.g., of a method, an application, a layer or an agent.

What is claimed is:

1. A method of dynamic biometric regulation of one or more IoT devices, comprising:

calibrating a dynamic IoT device setting module with user biomarker response to one or more IoT device settings;

monitoring one or more user biomarkers using the dynamic IoT device setting module;

storing the one or more user biomarkers in a user profile matrix;

detecting a first physiological state based upon the user profile matrix;

adjusting, in response to the existence of the first physiological state, one or more IoT device settings to settings associated with a second physiological state from the user profile matrix;
sensing user biomarker response to the adjusted settings;
determining if the sensed user biomarkers response align with the second physiological state; and
adjusting, in response to nonalignment of the sensed user biomarkers response with the second physiological state, the one or more IoT devices based upon a learning algorithm applied to the sensed user biomarker response by a learned behavior analysis unit coupled to a projection unit within the dynamic IoT device setting module until alignment of the sensed user biomarkers response with the second physiological state occurs;
wherein the learning algorithm comprises asymmetric dual-path processing guided by a set of switches for enabling a first mode of operation through a first route associated with a pattern recognition technique, a second mode of operation through a second route associated with Convolution Neural Network (CNN) processing, and a third mode of operation through a hybrid route associated with the first route and the second route, whereby each route produces an output used by the projection unit to generate IoT settings associated with transitioning the user to the second physiological state.

2. The method of claim 1, wherein calibrating a dynamic IoT device setting module comprises,
receiving user input defining the first physiological state and the second physiological state;
retrieving a first set of model biomarkers associated with the first physiological state and a second set of model biomarkers associated with the second physiological state from a model database;
retrieving one or more IoT device settings associated with the first physiological state and with the second physiological state from a model database;
storing user input, the first set of model biomarkers, the second set of model biomarkers, and the retrieved IoT device settings in the user profile matrix;
adjusting one or more IoT device settings to the retrieved one or more IoT device settings associated with the second physiological state;
monitoring user biomarker response to the adjusted one or more IoT device settings;
detecting if the monitored user biomarker response aligns with the second set of model biomarkers associated with the second physiological state;
adjusting, in response to nonalignment of the monitored user biomarkers, one or more IoT devices based upon the retrieved one or more IoT device settings associated with the second physiological state until the monitored user biomarker response aligns with the second physiological state; and
storing monitored user biomarker response in the user profile matrix.

3. The method of claim 1, wherein monitoring one or more user biomarkers comprises,
retrieving the user's temperature from a thermistor;
retrieving the user's blood pressure from a heart rate sensing unit having a deep learning algorithm;
retrieving the user's blood oxygen level from a pulse oximeter blood oxygen sensor;
retrieving the user's pulse from an optical heart sensor;
retrieving the user's blood glucose levels from a non-invasive glucose monitor; and
repeating the retrieving until a stop command is issued.

4. The method of claim 3, wherein storing one or more user biomarkers in a user profile matrix comprises,
storing the user temperature, blood pressure, blood oxygen level, blood glucose levels, and pulse in the user profile matrix.

5. The method of claim 1, wherein detecting a first physiological state based upon the user profile matrix comprises,
retrieving a first set of model biomarkers associated with the first physiological state from the user profile matrix;
comparing the monitored one or more user biomarkers with the first set of model biomarkers;
detecting a match of the monitored one or more user biomarkers with the first set of model biomarkers; and
setting a first flag, when the match occurs.

6. The method of claim 1, wherein adjusting the one or more IoT device settings associated with a second physiological state comprises,
retrieving the one or more IoT device settings associated with the second physiological state from the user profile matrix; and
modifying the setting of the one or more IoT devices to match the retrieved one or more IoT device settings.

7. The method of claim 6, wherein modifying the setting of the one or more IoT devices comprises:
adjusting a thermostat to align with one or more temperature settings of the second physiological state from the user profile matrix;
changing a displayed image on an electronic surface to align with the second physiological state;
changing a broadcasted audio to align with the second physiological state;
changing a broadcasted video to align with the second physiological state;
adjusting a light switch dimmer to align with the second physiological state; and
updating user profile matrix.

8. The method of claim 1, wherein determining if the sensed biomarkers align with the second physiological state comprises,
retrieving a second set of model biomarkers associated with the second physiological state from the user profile matrix;
comparing the sensed user biomarker response with the second set of model biomarkers;
detecting a match of the sensed user biomarker response with the second set of model biomarkers; and
setting a second flag, when the match occurs.

9. The method of claim 1, wherein adjusting one or more IoT devices based upon the learning algorithm until alignment of the sensed user biomarkers with the second physiological state occurs for the hybrid route comprises,
retrieving a model set of user biomarker responses associated with the second physiological state from a datastore;
extracting a set of one or more abridged matrices from the user profile matrix;
selecting a first matrix from the extracted set;
processing the first matrix using a Convolution Neural Network (CNN);
extracting a second matrix from the CNN processed matrix;

detecting the similarity between the second matrix and the retrieved model set of user biomarker responses using a pattern recognition technique;
projecting a next set of one or more IoT device settings based upon the similarity;
modifying the one or more IoT devices settings to match the next set;
sensing user biomarker response to the modified IoT device settings;
determining if the sensed user biomarkers align with the model set of user biomarker responses; and
repeating the projecting, modifying, sensing, and determining step until sensed user biomarkers align with the second physiological state.

10. The method of claim 1, wherein adjusting one or more IoT devices based upon the learning algorithm until alignment of the sensed user biomarkers with the second physiological state occurs for the first route comprises,
retrieving a model set of user biomarker responses associated with the second physiological state from a datastore;
detecting the similarity between the sensed user biomarkers and the retrieved model set of user biomarker responses using a pattern recognition technique;
projecting a next set of one or more IoT device settings based upon the similarity;
modifying the one or more IoT devices settings to match the next set;
sensing user biomarker response to the modified IoT device settings;
determining if the sensed user biomarkers align with the model set of user biomarker responses; and
repeating the projecting, modifying, sensing, and determining step until sensed user biomarkers align with the second physiological state.

11. The method of claim 1, wherein adjusting one or more IoT devices based upon the learning algorithm until alignment of the sensed user biomarkers with the second physiological state occurs for the second route comprises,
retrieving a model set of user biomarker responses associated with the second physiological state from a datastore;
extracting a set of one or more abridged matrices from the user profile matrix;
selecting a first matrix from the extracted set;
processing the first matrix using a Convolution Neural Network (CNN);
detecting the similarity between the CNN processed first matrix and the retrieved model set of user biomarker responses using a pattern recognition technique;
projecting a next set of one or more IoT device settings based upon the similarity;
modifying the one or more IoT devices settings to match the next set;
sensing user biomarker response to the modified IoT device settings;
determining if the sensed user biomarkers align with the model set of user biomarker responses; and
repeating the projecting, modifying, sensing, and determining step until sensed user biomarkers align with the second physiological state.

12. A dynamic physiological regulation system comprising:
a memory;
a processor coupled to the memory, the processor operable to implement a dynamic biometric agent, the dynamic biometric agent is operable to:
calibrate a dynamic IoT device setting module with user biomarker response to one or more IoT device settings defined within a user profile matrix;
monitor one or more user biomarkers;
store the one or more user biomarkers in a user profile matrix;
detect a first physiological state based upon the user profile matrix;
adjust, in response to the existence of the first physiological state, one or more IoT device settings to settings associated with a second physiological state from the user profile matrix;
sense user biomarker response to the adjusted settings;
determine if the sensed user biomarker response align with the second physiological state; and
adjust, in response to nonalignment of the sensed user biomarker response with the second physiological state, the one or more IoT devices based upon a learning algorithm applied to the sensed user biomarker response by a learned behavior analysis unit coupled to a projection unit within the dynamic biometric agent until alignment of the sensed user biomarker response with the second physiological state occurs;
wherein the learning algorithm comprises asymmetric dual-path processing guided by a set of switches for enabling a first mode of operation through a first route associated with a pattern recognition technique, a second mode of operation through a second route associated with Convolution Neural Network (CNN) processing, and a third mode of operation through a hybrid route associated with the first route and the second route, whereby each route produces an output used by the dynamic biometric agent to generate IoT settings associated with transitioning the user to the second physiological state.

13. The dynamic physiological regulation system of claim 12, wherein the dynamic biometric agent comprises,
an operation module coupled to receive user input defining a preferred physiological state;
a dynamic IoT controller coupled to the operation module and the one or more sensors to receive user input and sensed user biomarker data for detecting a current physiological state and generating one or more signals for altering the one or more IoT devices to shift the user to the preferred physiological state; and
a policy manager coupled to the dynamic IoT controller and memory to generate input for the dynamic IoT controller based upon policy data in alignment with the user profile matrix, the policy manager having associated security policies aligned with privacy and health laws, safety policies aligning with user's medical prognosis, IoT controller policies, and physiological state polices aligned with user health.

14. The dynamic physiological regulation system of claim 13, wherein the dynamic Iot controller comprises,
a biomarker detection unit coupled to retrieve input from a clinician monitored client node and the one or more sensors to detect whether the user's physiological state aligns with the preferred physiological state, the biomarker detection unit coupled to retrieve a set of model biomarkers associated with the preferred physiological state from a clinical datastore;
the learned behavior analysis unit coupled to the memory and the biomarker detection unit to extract a set of one or more abridged matrices of biomarkers from the user profile matrix and process the extracted set using CNN to make a determination of the similarity between the sensed user biomarker data and the data associated with the user profile matrix using pattern detection of repeated patterns in alignment with the current physiological state and a preferred physiological state; and the projection unit coupled to receive output from the learned behavior analysis unit to conduct predictive analysis for setting the one or more Iot device settings based upon the output of the learned behavior analysis unit.

15. A non-transitory computer-readable medium including code for performing a method of dynamic physiological regulation, the method comprising:

calibrating a dynamic IoT device setting module with user biomarker response to one or more IoT device settings defined within a user profile matrix;

monitoring one or more user biomarkers;

storing the one or more user biomarkers in a user profile matrix;

detecting a first physiological state based upon the user profile matrix;

adjusting, in response to the existence of the first physiological state, one or more IoT device settings to settings associated with a second physiological state;

sensing user biomarker response to the adjusted settings;

determining if the sensed user biomarkers response align with the second physiological state; and adjusting, in response to nonalignment of the sensed user biomarkers response with the second physiological state, the one or more IoT devices based upon a learning algorithm applied to the sensed user biomarker response by a learned behavior analysis unit coupled to a projection unit within the dynamic IoT device setting module until alignment of the sensed user biomarkers response with the second physiological state occurs;

wherein the learning algorithm comprises asymmetric dual-path processing guided by a set of switches for enabling a first mode of operation through a first route associated with a pattern recognition technique, a second mode of operation through a second route associated with Convolution Neural Network (CNN) processing, and a third mode of operation through a hybrid route associated with the first route and the second route, whereby each route produces an output used by the projection unit to generate IoT settings associated with transitioning the user to the second physiological state.

16. The computer-readable medium of claim 15, wherein calibrating a dynamic IoT device setting module comprises, receiving user input defining the first physiological state and the second physiological state;

retrieving a first set of model biomarkers associated with the first physiological state and a second set of model biomarkers associated with the second physiological state from a model database;

retrieving one or more IoT device settings associated with the first physiological state and with the second physiological state from a model database;

storing user input, the first set of model biomarkers, the second set of model biomarkers, and the retrieved IoT device settings in the user profile matrix;

adjusting one or more IoT device settings to the retrieved one or more IoT device settings associated with the second physiological state;

monitoring user biomarker response to the adjusted one or more IoT device settings;

detecting if the monitored user biomarker response aligns with the second set of model biomarkers associated with the second physiological state;

adjusting, in response to nonalignment of the monitored user biomarkers, one or more IoT devices based upon the retrieved one or more IoT device settings associated with the second physiological state until the monitored user biomarker response aligns with the second physiological state; and storing monitored user biomarker response in the user profile matrix.

17. The computer-readable medium of claim 15, wherein monitoring one or more user biomarkers comprises, retrieving the user's temperature from a thermistor;

retrieving the user's blood pressure from a heart rate sensing unit having a deep learning algorithm;

retrieving the user's blood oxygen level from a pulse oximeter blood oxygen sensor;

retrieving the user's pulse from an optical heart sensor;

retrieving the user's blood glucose levels from a non-invasive glucose monitor; and repeating the retrieving until a stop command is issued.

18. The computer-readable medium of claim 15, wherein detecting a first physiological state based upon the user profile matrix comprises, retrieving a first set of model biomarkers associated with the first physiological state from the user profile matrix;

comparing the monitored one or more user biomarkers with the first set of model biomarkers;

detecting a match of the monitored one or more user biomarkers with the first set of model biomarkers; and setting a first flag, when the match occurs.

19. The computer-readable medium of claim 15, wherein determining if the sensed biomarkers align with the second physiological state comprises, retrieving a second set of model biomarkers associated with the second physiological state from the user profile matrix;

comparing the sensed user biomarker response with the second set of model biomarkers;

detecting a match of the sensed user biomarker response with the second set of model biomarkers; and setting a second flag, when the match occurs.

20. The computer-readable medium of claim 15, wherein adjusting one or more IoT devices based upon a learning algorithm until alignment of the sensed biomarkers with the second physiological state occurs comprises, retrieving a set of model biomarkers associated with the second physiological state from a datastore;

extracting a set of one or more abridged matrices from the user profile matrix;

selecting a first matrix from the extracted set;

processing the first matrix using a CNN;

extracting a second matrix from the CNN processed matrix;

detecting the difference between the second matrix and the user profile matrix using a pattern recognition technique, selected from the group including Principal Component Analysis (PCA) and Linear Discriminate Analysis (LDA);

projecting a model set of one or more IoT device settings based upon the difference;

modifying the one or more IoT devices settings to match the model set;

sensing user biomarker response to the modified IoT device settings;

determining if the sensed user biomarkers align with the second physiological state; and repeating the projecting, modifying, sensing, and determining step until sensed user biomarkers align with the second physiological state.

\* \* \* \* \*